United States Patent [19]
Brennan et al.

[11] Patent Number: 6,111,110
[45] Date of Patent: Aug. 29, 2000

[54] SYNTHESIS OF BENZO[F]QUINOLINONES

[75] Inventors: John Brennan; Christopher William Doecke; Perry Clark Heath; Lawrence Edward Patterson; Uko Effiong Udodong; Leland Otto Weigel, all of Indianapolis, Ind.

[73] Assignee: Eli Lilly and Company, Indianapolis, Ind.

[21] Appl. No.: 09/254,829

[22] PCT Filed: Oct. 27, 1997

[86] PCT No.: PCT/US97/19229

§ 371 Date: Mar. 12, 1999

§ 102(e) Date: Mar. 12, 1999

[87] PCT Pub. No.: WO98/18757

PCT Pub. Date: May 7, 1998

Related U.S. Application Data

[60] Provisional application No. 60/027,868, Oct. 30, 1996.

[51] Int. Cl.$^7$ ...................... C07D 221/06; C07D 498/00
[52] U.S. Cl. .............................................. 546/110; 546/82
[58] Field of Search ....................... 546/110, 82

[56] References Cited

U.S. PATENT DOCUMENTS

| | | | |
|---|---|---|---|
| 5,239,075 | 8/1993 | Audia | 546/110 |
| 5,334,767 | 8/1994 | Audia | 568/327 |
| 5,550,134 | 8/1996 | Audia et al. | 514/284 |
| 5,629,007 | 5/1997 | Audia | 424/423 |
| 5,635,197 | 6/1997 | Audia | 424/423 |
| 5,670,512 | 9/1997 | Audia | 514/290 |
| 5,710,163 | 1/1998 | Audia | 514/290 |

FOREIGN PATENT DOCUMENTS

| | | |
|---|---|---|
| 0 703 221 A1 | 3/1996 | European Pat. Off. |
| 0 733 365 A1 | 9/1996 | European Pat. Off. |

OTHER PUBLICATIONS

Young et al, *The Methyl Group as a Protecting Group for Arylthiols: A Mild and Efficient Method for the Conversation of Methyl Aryl Sulfides to Arylthiols;* 25:17, 1753–1756 (1984).

Chem. Abstr., vol. 126, No. 1, Jan. 6, 1997, p. 891, col. 1, Abst. No. 8006x.

Chem. Abstr., vol. 125, No. 1, Jul. 1, 1996, p. 1170, col. 1, Abst. No. 10633x.

*Primary Examiner*—D. Margaret Seaman
*Attorney, Agent, or Firm*—Michael J. Sayles

[57] ABSTRACT

A process for preparing intermediates and benzoquinolin-3-one pharmaceuticals, such pharmaceuticals are effective in treating conditions consequent on 5α-reductase.

21 Claims, No Drawings

SYNTHESIS OF BENZO[F]QUINOLINONES

This application is a 371 of PCT/US97/19229, filed Oct. 27, 1997, claims benefit to U.S. provisional application Ser. No. 60/027,868 filed Oct. 30, 1996.

The present invention belongs to the fields of organic chemistry, pharmaceutical chemistry and chemical manufacture, and provides a convenient and economical process for preparing benzo[f]quinolinones which are useful as 5α-reductase inhibitors and provides intermediate compounds for the preparation of such pharmaceuticals.

A currently active field of pharmaceutical research is the inhibition of 5α-reductase, the enzyme which converts testosterone to dihydro-testosterone, a more potent androgen. It has been demonstrated that inhibitors of 5α-reductase can block the formation of dihydrotestosterone and ameliorate a number of highly undesirable conditions, including male pattern baldness and benign prostatic hypertrophy. Audia et al., have disclosed a series of benzo[f]quinolinone compounds which are 5a-reductase inhibitors. See: U.S. Pat. Nos. 5,239,075 and 5,541,190; *Tet. Let.,* 44, 7001 (1993); *J. Med. Chem.,* 36, 421 (1993); and European Patent Publication 0703221.

The present invention provides a novel process for preparing benzo[f]quinolinones which are effective inhibitors of 5α-reductase. The present process is more efficient than prior processes, is amenable to large-scale synthesis, and avoids the formation of unwanted by-products. This invention also provides intermediate compounds for the preparation of such pharmaceuticals.

The present invention provides a novel process for preparing benzo[f]quinolinones and provides intermediates useful in preparing benzo[f]quinolinones. More specifically, the present invention is directed to a process for preparing a compound of the formula I

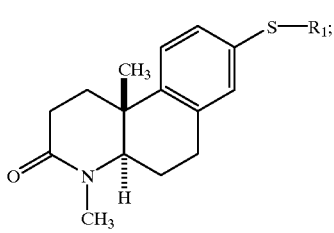

I wherein $R^1$ represents:
2-nitrophenyl, 4-nitrophenyl, 2-cyanophenyl, 4-cyanophenyl, 2-nitronaphthyl, 4-nitronaphthyl, 2-cyanonaphthyl, 4-cyanonaphthyl, 2-quinolinyl, 4-quinolinyl, 7-quinolinyl, 1-isoquinolinyl, 3-isoquinolinyl, 8-isoquinolinyl, 2-quinoxalinyl,
2-benzothiazolyl, 3-1H-indazolyl, 2-benzoxazolyl, 3-1,2-benzoisothiazolyl, 2-pyridinyl, 4-pyridinyl, 2-pyrazinyl, 2-naphtho[2,3]-dithiazolyl, 2-naphtho[1,2-d]thiazolyl, 9-anthryl, 2-thiazolyl, 2-benzimidazolyl, 1-benz[g]isoquinolinyl, 8-benz[g]isoquinolinyl, 5-1H-tetrazolyl, 2-quinazolinyl, 2-thiazolo[4,5-b]pyridinyl, 4-10H-pyridazino[3,2-b]-2-quinazolinyl, 2-1,4-benzodioxinyl, 2-triazine, 2-benzoxazine, 4-benzoxazine, 2-purine or 8-purine;

wherein the above $R^1$ groups are unsubstituted or substituted with 1–3 functionalities chosen from the group consisting of trifluoromethyl, trifluoroethoxy, $C_1$–$C_4$ alkyl, trifluoromethoxy, hydroxy, $C_1$–$C_3$ alkoxy, nitro, $C_1$–$C_3$ alkylthio, $C_1$–$C_6$ alkanoyl, phenyl, oxo, phenoxy, phenylthio, $C_1$–$C_3$ alkylsulfinyl, $C_1$–$C_3$ alkylsulfonyl, cyano, amino, $C_1$–$C_3$ alkylamino, diphenylmethylamino, triphenylmethylamino, benzyloxy, benzylthio, (mono-halo, nitro or $CF_3$)benzyl(oxy or thio), di($C_1$–$C_3$ alkyl, $C_3$–$C_6$ cycloalkyl, or $C_4$–$C_8$ cycloalkylalkyl)amino, (mono-$C_1$–$C_3$ alkyl, $C_1$–$C_3$ alkoxy or halo)(phenyl, phenoxy, phenylthio, phenylsulfonyl or phenoxysulfonyl), $C_2$–$C_6$ alkanoylamino, benzoylamino, diphenylmethylamino($C_1$–$C_3$ alkyl), aminocarbonyl, $C_1$–$C_3$ alkylaminocarbonyl, di($C_1$–$C_3$ alkyl) aminocarbonyl, halo-$C_1$–$C_6$ alkanoyl, aminosulfonyl, $C_1$–$C_3$ alkylaminosulfonyl, di($C_1$–$C_3$ alkyl)aminosulfonyl, phenyl(oxy or thio)($C_1$–$C_3$ alkyl), (halo, $C_1$–$C_3$ alkyl or $C_1$–$C_3$ alkoxy)phenyl(oxy or thio)($C_1$–$C_3$ alkyl), benzoyl, or (amino, $C_1$–$C_3$ alkylamino or di($C_1$–$C_3$ alkyl)amino)($C_1$–$C_3$ alkyl).

An aspect of the invention comprises: converting a ketone of the formula

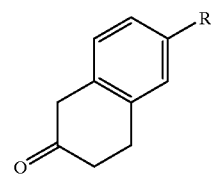

wherein R is halogen, preferably bromo or iodo;

to a protected ketal, preferably employing trimethylsilyltrifluoromethanesulfonate and 1,3-bis-trimethylsilyloxy propandiol in methylene chloride;

reacting the protected ketal with a reactive alkyllithium compound, such as, n-butyllithium and a sulfur transfer reagent, such as, dimethyl disulfide, to afford an S-methylated ketal compound; and deprotecting the S-methylated ketal compound to afford a methyl-thiotetralone compound of the formula II

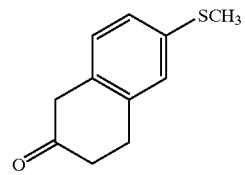

II

Another aspect of the invention comprises preparing the compound of formula II

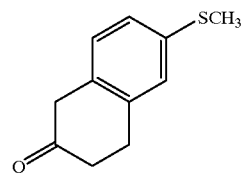

II by reacting a compound of the formula

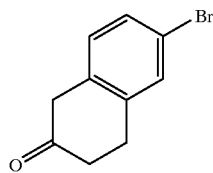

with lithium diisopropylamide, n-butyllithium and dimethyl disulfide or by converting a compound of the formula XI

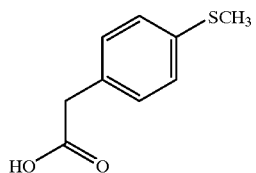

XI to an acid halide, for example, an acid chloride; reacting the acid chloride with a Lewis acid and ethylene to afford the compound of formula II.

According to another aspect, the invention comprises converting the compound of formula II to a compound of the formula I. One such preferred process comprises reacting the compound of formula II with (R)-(+)-phenethylamine to afford a compound of the formula III

III

[Structure of compound III]

reacting the compound of formula III with a strong lithium base to afford a lithioenamine compound of the formula IV

IV

[Structure of compound IV]

methylating the resulting lithioenamine of the formula IV to a compound of the formula V, for example, by reacting the resulting lithioenamine with methyl iodide in an ether solvent to prepare the compound of formula V

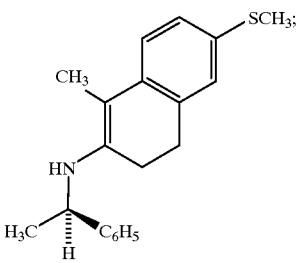

V reacting the compound of formula V with an acyl halide or an anhydride of acrylic acid to prepare a compound of the formula VI

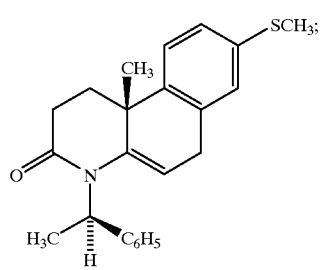

VI quenching the reaction with base, and combining the residue comprising the compound of formula VI with an appropriate silane and trifluoroacetic acid in the absence of a solvent to prepare a compound of the formula VII

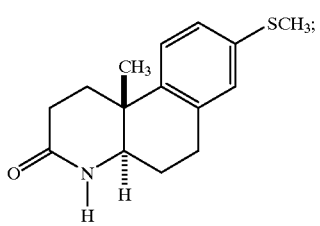

VII reacting the compound of formula VII with a methyl halide, for example, methyl iodide in a reaction mixture comprising an organic solvent and a strong base to afford an arylmethylsulfide compound of the formula VIII

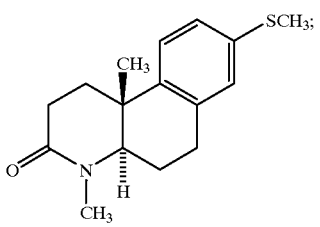

VIII oxidizing the compound of formula VIII to a sulfoxide compound of the formula IX

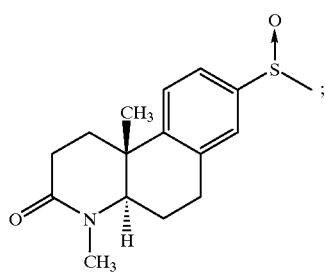

IX reacting the sulfoxide compound of the formula IX with an acylating agent to afford a Pummerer rearrangement product; reacting the Pummerer rearrangement product with an electrophile selected from the group consisting of A-R$^1$ wherein A is a leaving group and R$^1$ represents: 2-nitrophenyl, 4-nitrophenyl, 2-cyanophenyl, 4-cyanophenyl, 2-nitronaphthyl, 4-nitronaphthyl, 2-cyanonaphthyl, 4-cyanonaphthyl, 2-quinolinyl, 4-quinolinyl, 7-quinolinyl, 1-isoquinolinyl, 3-isoquinolinyl, 8-isoquinolinyl, 2-quinoxalinyl, 2-benzothiazolyl, 3-1H-indazolyl, 2-benzoxazolyl, 3-1,2-benzisothiazolyl, 2-pyridinyl, 4-pyridinyl, 2-pyrazinyl, 2-naphtho[2,3-d]thiazolyl, 2-naphtho[1,2-d]thiazolyl, 9-anthryl, 2-thiazolyl, 2-benzimidazolyl, 1-benz[g]isoquinolinyl, 8-benz[g]isoquinolinyl, 5-1H-tetrazolyl, 2-quinazolinyl, 2-thiazolo[4,5-b]pyridinyl, 4-10H-pyridazino[3,2-b]-2-quinazolinyl, 2-1,4-benzodioxinyl, 2-triazine, 2-benzoxazine, 4-benzoxazine, 2-purine or 8-purine;

wherein the above R$^1$ groups are unsubstituted or substituted with 1–3 groups chosen from the group consisting of trifluoromethyl, trifluoroethoxy, $C_1$–$C_4$ alkyl, trifluoromethoxy, hydroxy, $C_1$–$C_3$ alkoxy, nitro, $C_1$–$C_3$ alkylthio, $C_1$–$C_6$ alkanoyl, phenyl, oxo, phenoxy, phenylthio, $C_1$–$C_3$ alkylsulfinyl, $C_1$–$C_3$ alkylsulfonyl, cyano, amino, $C_1$–$C_3$ alkylamino, diphenylmethylamino, triphenylmethylamino, benzyloxy, benzylthio, (mono-halo, nitro or CF$_3$)benzyl(oxy or thio), di($C_1$–$C_3$ alkyl, $C_3$–$C_6$ cycloalkyl, or $C_4$–$C_8$ cycloalkylalkyl)amino, (mono-$C_1$–$C_3$ alkyl, $C_1$–$C_3$ alkoxy or halo)(phenyl, phenoxy, phenylthio, phenylsulfonyl or phenoxysulfonyl), $C_2$–$C_6$ alkanoylamino, benzoylamino, diphenylmethylamino($C_1$–$C_3$ alkyl), aminocarbonyl, $C_1$–$C_3$ alkylaminocarbonyl, di($C_1$–$C_3$ alkyl)aminocarbonyl, halo-$C_1$–$C_6$ alkanoyl, aminosulfonyl, $C_1$–$C_3$ alkylaminosulfonyl, di($C_1$–$C_3$ alkyl)aminosulfonyl, phenyl(oxy or thio)($C_1$–$C_3$ alkyl), (halo, $C_1$–$C_3$ alkyl or $C_1$–$C_3$ alkoxy)phenyl(oxy or thio)($C_1$–$C_3$ alkyl), benzoyl, or (amino, $C_1$–$C_3$ alkylamino or di($C_1$–$C_3$ alkyl)amino)($C_1$–$C_3$ alkyl);

in the presence of a phase transfer catalyst, ahydride reducing reagent and a base, to prepare a compound of formula I.

According to another aspect of the invention, the compound of formula VIII

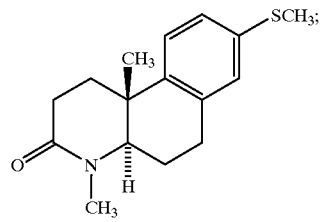

VIII is prepared by the process which comprises reacting a compound of the formula XII

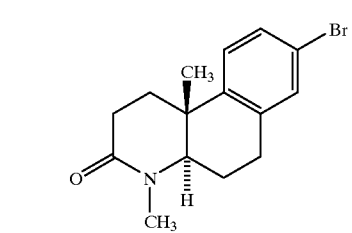

XII with a reaction mixture comprising a base, such as lithium diisopropylamide or lithium hexamethyldisilazide, and an ether solvent to afford an amide-enolate solution; reacting the amide-enolate solution with an alkyllithium compound to afford a dianion compound of the formula

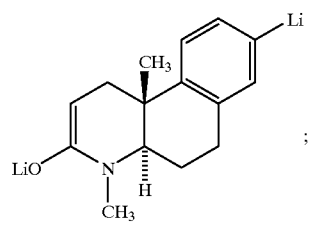

reacting the dianion compound with dimethyldisulfide to afford an arylmethylsulfide compound of the formula VIII.

The preferred intermediates of the present invention have the formulas II, VI and VIII:

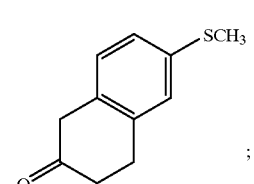

II

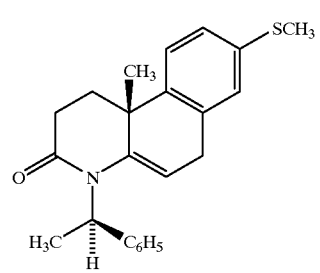

VI

-continued
and

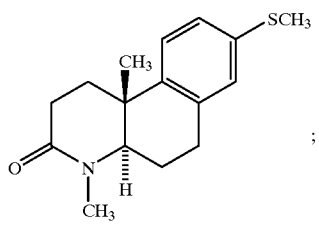

VIII or salts thereof.

Starting materials for the compounds in the claimed process are either commercially available, known in the art, or can be prepared by methods known in the art, for example, see. Audia et al. in U.S. Pat. No. 5,239,075, issued Aug. 24, 1993 and European Patent Publication 0703221.

Throughout this document, all temperatures will be described in degrees Celsius and all expressions of concentration, percentage and proportion will be expressed in weight units, except for mixtures of solvents, which will be described in volume units, unless otherwise stated.

References to compounds in this document include the pharmaceutically acceptable salts of such compounds, unless otherwise stated.

The various positions on the benzo[f]quinoline ring are indicated below.

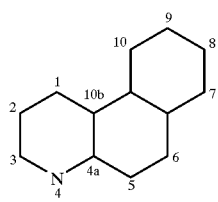

The spatial configuration of the group at 10b and the hydrogen atom at 4a are required. The reader will understand that many of the compounds can exist in two or more stereochemical forms, and that all stereochemical forms are included in the present invention. In some of the compounds prepared or described below, single enantiomers are prepared in pure form and are identified by (+) or (−) nomenclature. In other cases, the mixture of diastereomers is prepared.

The group S-$R^1$ occupies the 8 position.

The term "halogen" and "halo" includes chloro, bromo, fluoro and iodo.

The various alkyl groups, such as $C_1$–$C_4$ alkyl and the like include groups such as methyl, ethyl, propyl, isopropyl, t-butyl, n-butyl and isobutyl. Alkenyl and alkynyl groups constitute linking groups which are bivalent and are bonded to two other groups. For example, $C_2$–$C_4$ alkenyl includes ethenyl, 2-propenyl, 3-butenyl and 2-butenyl; and $C_2$–$C_4$ alkynyl includes, for example, ethynyl, 2-propynyl, 2-butynyl and iso-2-butynyl.

The group $C_1$–$C_6$ alkanoyl includes such groups as formyl, acetyl, propionyl, isobutyryl, 2-ethylpropionyl and hexanoyl. The group $C_3$–$C_6$ cycloalkyl includes cyclopropyl, cyclobutyl, cyclopentyl and cyclohexyl, and the group $C_4$–$C_8$ cycloalkylalkyl includes, for example, cyclopropylmethyl, cyclohexylethyl, cyclobutylbutyl and cyclohexylmethyl.

Terms such as halo-$C_1$–$C_6$ alkanoyl, halophenyl or $C_1$–$C_3$ alkylphenyl refer to the indicated basic group having substituted on it 1, 2, or 3 halo or $C_1$–$C_3$ alkyl groups as may be described in the individual case.

The present process prepares compounds of formula I all having the benzo[f]quinoline nucleus, on the benzo ring of which is substituted a cyclic group $R^1$ linked to the benzoquinoline through a sulfur linker. The $R^1$ groups may be substituted with additional organic groups, and may bear as many as three of the indicated substituent groups. Multiple substituents may all be the same or may be different.

Certain aspects of the process are preferred and will be mentioned below specifically. It will be understood that the following aspects are each important individually, and also that preferred aspects may be combined to create further, more limited or more expansive, preferred aspects.

Synthesis of 6-Methylthio-2-tetralone

The starting material for the synthesis of 6-methylthio-2-tetralone is 4-methylthiophenylacetic acid.

4-methylthiophenylacetic acid is commercially available (Aldrich Catalog Handbook of Fine Chemicals 1994–5, page 1000) or may be prepared by procedures well-known to those skilled in the art. For example, 4-methylthiophenylacetic acid may be prepared via the Kindler modification of the Willgerodt reaction. 4-methylthioacetophenone is combined with sulfur and a primary or secondary amine, preferably morpholine, followed by hydrolysis (Scheme I). Alternatively, 4-methylthiophenylacetic acid may be prepared by hydrolysis of the corresponding nitrile or in two steps from benzyl alcohol. (Scheme II).

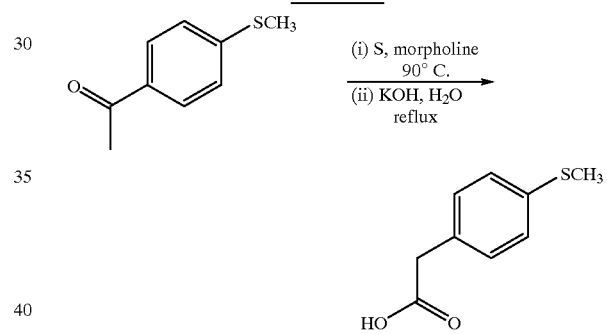

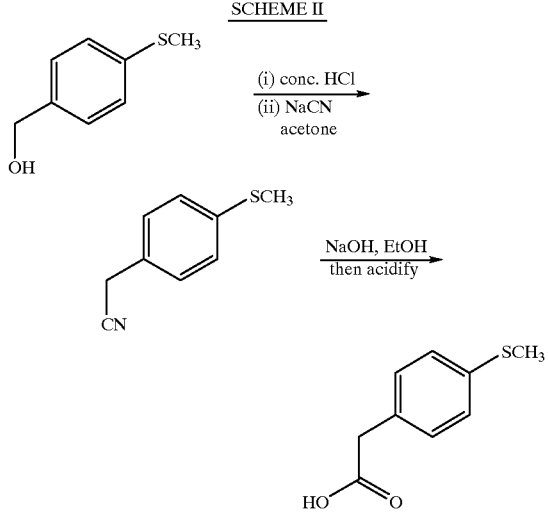

6-Methylthio-2-tetralone is prepared by reacting 4-methylthiophenylacetic acid with thionyl chloride, phosphorus trichloride, oxalyl chloride, or phosphorus pentachloride, under conditions known to those skilled in the art, to afford 4-methylthiophenacetyl chloride (Scheme III). Preferably thionyl chloride and N,N-dimethylformamide are employed to afford the 4-methylthiophenacetyl chloride. By a Friedel-Crafts acylation reaction of 4-methylthiophenacetyl chloride with ethylene gas in the presence of a Lewis acid catalyst and an inert or substantially inert solvent or mixture of solvents, ring closure is effected to afford the 2-tetralone II.

Addition of ethylene is exothermic in nature and temperatures from about −78° C. to about 30° C. are employed using standard cooling procedures. Significantly improved yields of 6-methylthio-2-tetralone were observed upon the simultaneous addition of the 4-methylthiophenacetylhalide and ethylene to methylene chloride and AlBr₃ at temperatures from about 5° C. to about −15° C.

Alternatively, preparation of 6-methylthio-2-tetralone may be afforded according to the following Scheme IV.

SCHEME IV

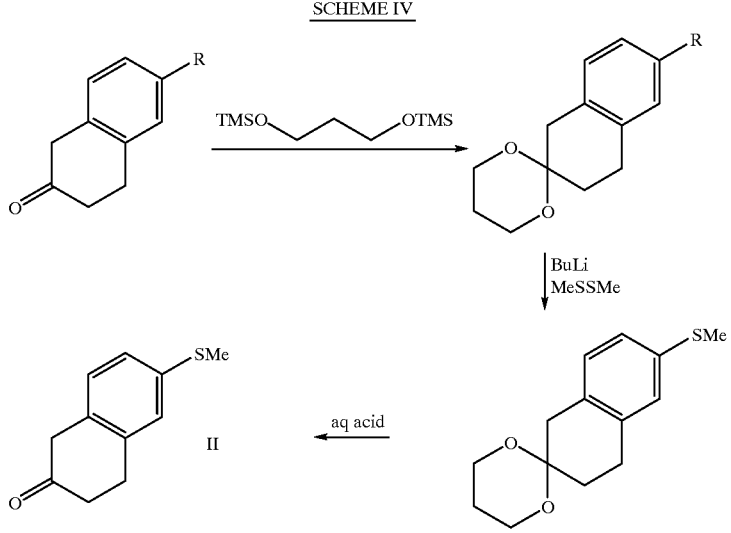

where R is halogen, preferably bromo.

The ketone group of the tetralone is first protected as a ketal. Preferably, ketalization is afforded by slowly adding 1,3-bis-trimethylsilyloxy propandiol to a solution of trifluromethanesulfonate in methylene chloride. Temperatures from about −70° C. to about −60° C. are employed using standard cooling procedures. For example, 6-bromo-2-tetralone is slowly added to a solution of 1,3-bis-trimethylsilyloxy propandiol and trifluromethanesulfonate in methylene chloride to yield 6-bromo-2-tetralone propylene ketal.

Halogen-metal exchange is then afforded by reacting the protected ketal with a reactive organolithium compound, preferably n-butyllithium. Alkylation of the resulting lithium species with an appropriate sulfur transfer reagent, for example, a sulfenyl halide or dimethyl disulfide affords a 6-methylthio-2-tetralone propylene ketal compound. Deprotection of the S-methylated ketal compound is afforded by treatment with aqueous acid, preferably hydrochloric acid, to afford the desired 6-methylthio-2-tetralone compound.

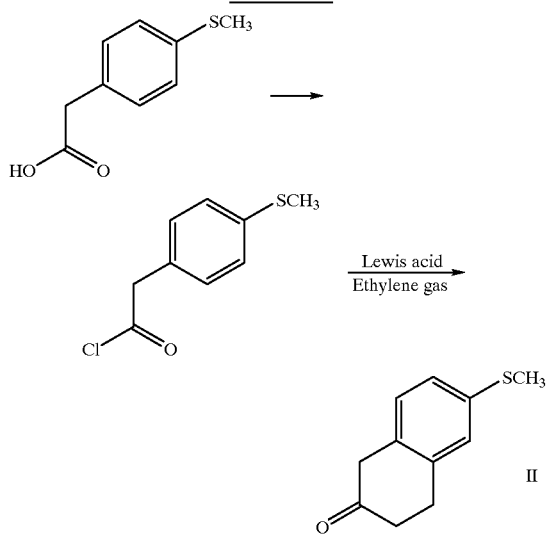

SCHEME III

Suitable Lewis acid catalysts include AlBr₃, AlCl₃, AlI₃, GaCl₃, FeCl₃, SbCl₅, ZrCl₄, SnCl₄, BCl₃, BF₃, SbCl₃ and the like, preferably, AlBr₃. Solvents used for this reaction include carbon disulfide, methylene chloride, nitromethane, 1,2-dichloroethane, nitrobenzene, and the like, preferably methylene chloride. The cyclization of thiomethyl tetralone requires rigorous conditions and is difficult to isolate. Improved yields of 6-methylthio-2-tetralone are achieved under rigorous conditions and employing AlBr3 as the Lewis acid. Cyclization is carried out at temperatures of about −78° C. to about 25° C., preferably less than 0° C.

Alkylation and Aza-annulation

A previous synthesis for the intermediate compound of the formula VII

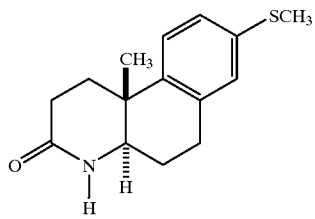

VII was taught in U.S. Pat. No. 5,239,075 and U.S. patent application Ser. No. 08/443,994, each of which is incorporated by reference herein. Another synthesis of the compound of formula VII, of which this invention constitutes an improvement, was shown in European Patent Publication 0564193. The methylthio group of the compound of formula VII is located at the 8-position. This preferred process of preparing the compound of formula VII, described below, can be carried out without purification or isolation of the intermediate products.

6-Thiomethyl-2-tetralone is reacted with (R)-(+)-phenethylamine to prepare the intermediate of the formula III

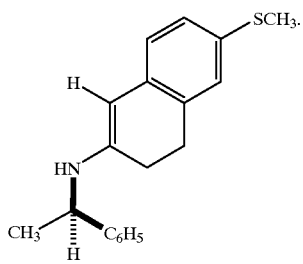

III

The reaction is conveniently carried out at elevated temperature, particularly the reflux temperature, in toluene in the presence of a strong acid such as p-toluenesulfonic acid. Water must be removed as it is formed in this reaction, and the absence of water being formed is an indication of completion of the reaction. A slight excess of phenethylamine, such as about 1.05–1.10 equivalents, should be used. Alternatively, tetrahydrofuran may be used as the solvent, and it is particularly convenient in that case to use molecular sieves to dehydrate the reaction mixture, using at least twice the weight of molecular sieves compared to the amount of water which will be released by the process.

The above phenethylamino compound is lithiated with, for example, n-butyllithium or with lithium diisopropylamide to afford a compound of the formula IV

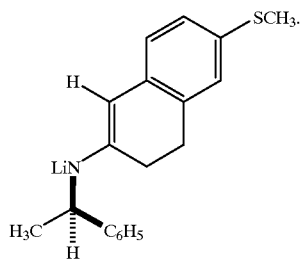

IV

When the reaction is carried out, as is preferred, with lithium diisopropylamide, the best results are obtained if the lithium diisopropylamide is freshly generated from diisopropylamine and n-butyllithium immediately before use in the process. A substantial excess, about 15–25%, of lithium diisopropylamide should be used for best results.

The lithium diisopropylamide reaction is best carried out in tetrahydrofuran at a low temperature in the range of about −100° to about 0°, preferably about −78° to about −10°. The phenethylamino compound need not be purified or isolated, but the first reaction mixture should be evaporated under vacuum and the residue taken up in tetrahydrofuran. It is preferred to add the phenethylamino material, in solution, to a solution of lithium diisopropylamide in cold tetrahydrofuran; the opposite manner of addition is operable but provides lower yields. In general, the reaction may be carried out in less than one hour.

The lithio compound is difficult to isolate and purify, and so it should be introduced into the process of the present invention as a solution in the lithiation reaction mixture.

Alkylation

The lithio compound is methylated, for example by reacting the resulting lithioenamine with methyl iodide to provide the compound of the formula V

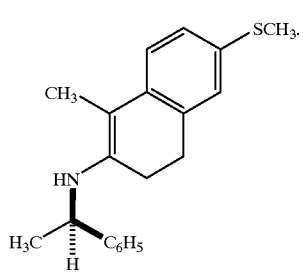

V

Dimethyl sulfate, methyl bromide, methyl chloride, methyl iodide, and the like, may be employed to methylate the lithioenamine. It is advisable to use about 15–25% of excess methyl iodide, and to carry out the process in a solvent, preferably an ether solvent, such as diethyl ether, methyl t-butyl ether or, preferably, tetrahydrofuran. The reaction is very rapid at low temperatures in the range of about −100° to about −50°, most preferably, about −80° to about −60°. Reaction times in the range of from about a few minutes to about one hour are adequate, and a 20 minute reaction time is preferred.

If the lithio compound is in the form of the reaction mixture from lithiation with lithium diisopropylamide, and the reaction mixture therefore contains the residual diisopropylamine, that amine must be neutralized before methylation. Most conveniently, the methyl iodide mixture is allowed to warm to a temperature close to 0°, and a sufficient amount of methanesulfonic acid is added to neutralize the diisopropylamine. Other strong acids may be used, but methanesulfonic acid is particularly convenient and preferred because the resulting methanesulfonate-salt of diisopropylamine is only slightly soluble and therefore may be easily removed by simple filtration or centrifugation.

Aza-Annulation Step

The reaction mixture comprising the compound of the formula V is combined with an acyl halide or an anhydride of acrylic acid or acryloyl chloride, or the like, to initiate the aza-annulation reaction which forms the compound of formula VI

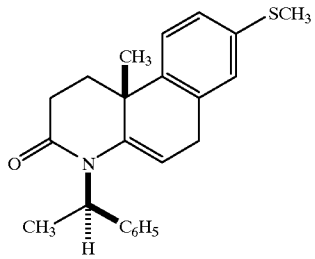

VI

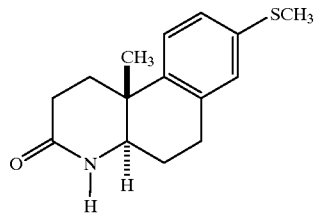

VII

It is best to generate the acrylic anhydride, the preferred reagent, immediately before use by the reaction of acryloyl chloride and acrylic acid, using triethylamine and a stabilizer, such as hydroquinone and butylated hydroxytoluene, in tetrahydrofuran.

The aza-annulation is best carried out by adding the acrylic anhydride or acryloyl chloride at a very low temperature, such as from about −100° to about −70°, and allowing the mixture to warm very slowly with stirring to a temperature in the range of about −20° to about 0°, or even up to about 10°−20°. A period of 12−15 hours is a reasonable period of time to allow the mixture to warm. When the reaction has gone as far toward completion as is desired, the reaction is quenched by addition of solid sodium bicarbonate. It is preferred to use from about 1.5 to about 4 equivalents of base, most preferably about 2 equivalents. The base may be added as a solution, for example, in water or in an aqueous solvent such as water/dimethylaminopyridine, but it is preferred to add the base in solid form. The reaction mixture is stirred with the quenching base for a brief period, and then the mixture is filtered, the volatiles are removed, and the solvent may be replaced with an ether solvent, preferably diethyl ether, and the organic solution may then be worked-up by washing with aqueous base and aqueous acid, and perhaps with additional purification steps such as a wash with a saturated salt solution. If such work-up steps are used, the solution is then dehydrated and evaporated under vacuum to obtain the non-volatile portions of the reaction mixture, containing the final intermediate of formula VI. On the other hand, the residue from the quenched reaction mixture may be carried on without work-up, if desired.

Reduction-Cleavage Step

The residue from the aza-annulation step is cooled, and a chilled mixture of an appropriate silane and trifluoroacetic acid is added. An appropriate silane being a soluble silane, for example, a dialkylsilane or trialkylsilane or the like. The addition should take place at a low temperature in the range of from about −40° to about 0°, and no other solvent is used. A large quantity of trifluoroacetic acid, in the range of about 10−50 equivalents, most preferably about 20−30 equivalents is used. The preferred trialkylsilane is triethylsilane, although trimethylsilane, tripropylsilane and the like may also be used. A substantial excess of trialkylsilane, in the range of about 5−20 equivalents, most preferably about 7−15 equivalents is used. The mixture is stirred for about 10−20 hours while it is allowed to warm slowly to about 30°, and then the mixture is slowly heated to an elevated temperature, preferably the reflux temperature, and is stirred at that temperature for a few hours, such as about 2−6 hours to complete the formation of the compound of formula VII Purification The residue containing the product of formula VII may be dissolved, preferably in a haloalkane such as dichloromethane, washed with base, such as aqueous sodium bicarbonate, and concentrated under vacuum. The residue may be thoroughly washed with, for example, an ether solvent, preferably diethyl ether, to obtain the purified compound of formula VII.

N-Alkylation Process

It is necessary in the synthesis to methylate the nitrogen at the 4 position on the benzo[f]quinoline ring. U.S. Pat. No. 5,239,075 shows such alkylation by reaction with an alkyl iodide in the presence of a strong base such as sodium hydride. An additional alkylation is shown in EPO publication 0703221.

The N-methylation comprises reacting a compound of the formula VII with a methyl halide, for example, methyl iodide in a reaction mixture comprising an organic solvent, for example a solvent chosen from the group consisting of tetrahydrofuran, dimethoxyethane, diethoxyethane and methyl t-butyl ether, and a base, for example, aqueous sodium or potassium hydroxide to afford a compound of the formula VIII

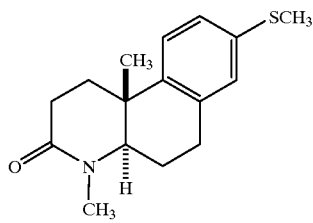

VIII

This alkylation process allows for an effective alkylation, under mild and easily controlled conditions, and allows for easy isolation of the products.

The alkylation process is carried out in conventional chemical plant equipment, preferably at ambient pressure and at moderate temperatures. It is preferably begun by slurrying the starting material of formula VII in the organic solvent at a temperature near ambient, such as from about 0° to about 50°, more preferably from about 15° to about 25°. The most preferred organic solvent is tetrahydrofuran, and it is preferred to use about 5−15 liters of solvent per kilogram of starting material; more preferable solvent volume is about 10 liters per kilogram. The alkyl iodide is then added as neat liquid. A substantial excess of alkyl iodide is preferably used, such as about 1.2−1.8 equivalents based on the starting material, most preferably about 1.5 equivalents.

The aqueous sodium or potassium hydroxide is then added, still at about ambient temperature, in an amount of about 1−4 liters per kilogram of starting material. The quantity of aqueous base is somewhat dependent on the concentration of the base and the choice of sodium or potassium hydroxide; when the most preferred base, 50% sodium hydroxide, is used, the most preferred amount of it is about 2 liters per kilogram of starting material. Then the reaction mixture, consisting of solid material slurried in two liquid phases, is warmed to about 25–650 with vigorous agitation and the reaction is allowed to proceed at about constant temperature with constant agitation. The preferred reaction temperature is about 35–40°. As the reaction proceeds toward completion, the solid starting material and alkyl iodide will dissolve and react, so the disappearance of solids is a crude indication of completion. The reaction may be followed by high pressure liquid chromatography on C-18 silica gel column, eluting with 1:1 acetonitrile:aqueous buffer (5% ammonium acetate) and monitoring at 220 nanometers.

When the reaction has gone as far as is desired toward completion, the mixture is cooled to about ambient and the aqueous layer is separated and discarded.

The preferred purification and isolation procedure proceeds by diluting the organic layer with water, and neutralizing it with aqueous mineral acid. Then the solution is distilled until the vapor temperature rises to about 69–80°, removing most of the tetrahydrofuran. Slow cooling to about 5° over a period of about 1–14 hours crystallizes the product, which needs only washing with water and drying to be ready for use as an intermediate or as a pharmaceutical.

The alkylation process provides product in the same stereochemical form as the starting material, in satisfactory purity for the pharmaceutical industry, and in yields of or above 90% when operated according to the preferred manners.

Thioalkylation

The compound of formula VIII may also be prepared via thiomethylation of (+)-(4aR)-(10bR)-4-methyl-8-halo-10b-methyl-1,2,3,4,4a,5,6,10b-octahydrobenzo[f]quinolin-3-one. Preferably, the amide enolate is afforded by combining (+)-(4aR)-(10bR)-4-methyl-8-bromo-10b-methyl-1,2,3,4,4a,5,6,10b-octahydrobenzo[f]quinolin-3-one with a lithium salt, for example, lithium chloride in an organic solvent, preferably tetrahydrofuran. A weak base, such as, lithium hexamethyldisilazide (LiN(TMS)2) is slowly added and the mixture is stirred at room temperature. Methyl lithium may be added to facilitate hexamethyldisilazide deprotonation. The reaction is then cooled to −70° C. and an alkyllithium compound, for example, n-butyllithium, is employed to aid in the formation of the dianion.

The amide-enolate solution may also be afforded by sequential treatment of (+)-(4aR)-(10bR)-4-methyl-8-halo-10b-methyl-1,2,3,4,4a,5,6,10b-octahydrobenzo[f]quinolin-3-one with a strong base, for example, lithium diisopropylamide in an ether solvent, preferably tetrahydrofuran, followed by lithium halogen exchange with aged n-butyllithium, sec-butyllithium or the like (Scheme V).

The dianion compound is then reacted with dimethyldisulfide to afford an arylmethylsulfide compound of formula VIII. A very high degree of chemoselectivity of the dianion with dimethyldisulfide was observed.

SCHEME V

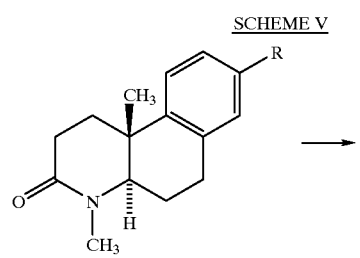

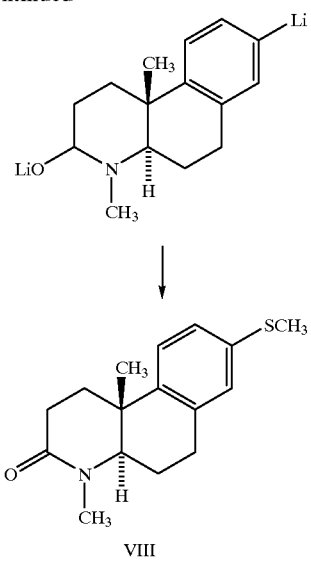

VIII wherein R is halogen, preferably bromo.

Electrophilic Coupling

The electrophilic coupling of the $R^1$ substituent to the sulfur group on the benzo[f]quinolinone ring may be afforded according to the following scheme VI.

SCHEME VI

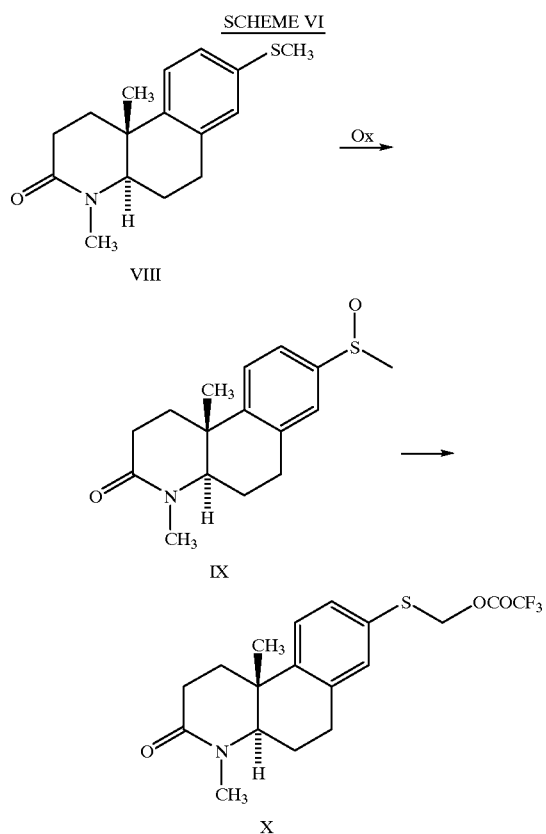

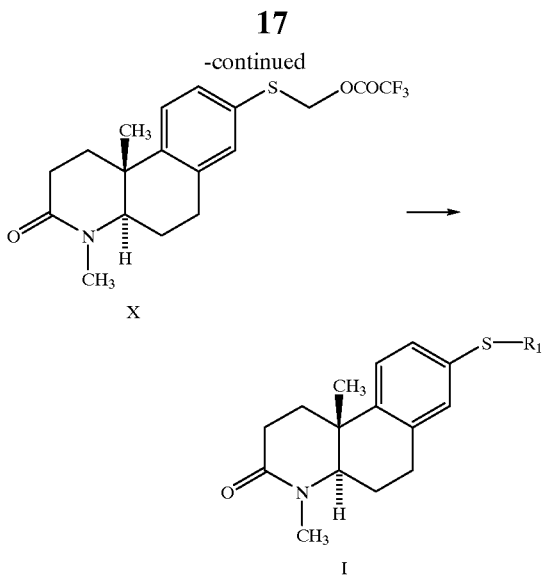

wherein R¹ is as defined above in formula I.

(+)-(4aR)-(10bR)-4-Methyl-8-methylthio-10b-methyl-1,2,3,4,4a,5,6,10b-octahydrobenzo[f]quinolin-3-one is oxidized to a sulfoxide compound. m-Chloroperoxybenzoic acid is a preferred oxidizing agent. With or without isolation, the sulfoxide compound is subjected to a Pummerer reaction as taught by Young, et al., *Tetrahedron Lett.* 25, 1753 (1984), such that the sulfoxide is reacted with an acylating agent, such as, trifluoroacetic anhydride to afford a trifluoroacetyloxymethylene sulfide compound. The trifluoroacetyloxymethylene sulfide compound is reacted with an electrophilic reagent, a hydride reducing reagent, such as sodium borohydride, potassium borohydride, lithium borohydride or the like, and a base, preferably a hydroxide or carbonate, most preferably, potassium carbonate, to prepare a compound of formula X. For the purpose of this reaction, suitable acylating agents include acyl halides, such as, acetyl chloride, sulfonic acid halides, reactive anhydrides, such as, trichloroacetic anhydride, phosphoric acid anhydride, sulfonic acid anhydride and like agents capable of yielding a Pummerer rearrangement product.

By methods known in the art, the electrophilic reagent is substituted with a leaving group, such as a halogen, sulfate, sulfonate or the like. The electrophilic reagent is then coupled to the sulfur on the benzo[f]quinolinone ring. A preferred electrophilic reagent is 2-chloro-4-ethylbenzothiazole and this reagent is coupled with the compound of formula X to afford (+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

Preferably a catalyst, for example tetrabutylammonium hydrogen sulfate is employed to direct the coupling of the trifluoroacetyloxymethylene sulfide with the electrophilic reagent. Sodium borohydride has been found to induce the reduction of the trifluoroacetyloxymethylene sulfide compound. Also, formaldehyde is generated in situ which is environmentally and pharmaceutically unacceptable. The present process reduces the formaldehyde as it is formed to methanol. Also, according to the present process, disulfides forming from air oxidation are reduced in situ. This process step allows starting materials to be more fully utilized and rigorous exclusion of oxygen, or impurities which promote oxidation, is unnecessary. Adding base to the mixture is not essential to promote the coupling. However, the decomposition of the borohydride is slowed, and the relative coupling rate is accelerated, with added base.

The following Preparations further illustrate the present inventive process. The Preparations are not intended to be limiting to the scope of the invention in any respect and should not be so construed.

Unless otherwise noted, starting materials were obtained from commercial suppliers and used without further purification. Toluene, dimethylformamide, and methylene chloride were stored over 4A molecular sieves. Tetrahydrofuran was distilled from sodium benzophenone ketyl. Reactions using organometallic reagents were run under nitrogen. Reactions were monitored by high pressure liquid chromatography using the conditions specified below. Thin layer chromatography was done using Merck plates of Silica Gel 60 with a fluorescent indicator ($F_{254}$). $^1$H and $^{13}$C NMR spectra were recorded on a General Electric QE or Bruker 300 MHz spectrophotometer at ambient temperature using $CDCl_3$ as solvent unless specified otherwise. NMR chemical shifts were recorded in ppm with solvent as the internal standard on the d scale and J values are in Hertz. IN, UV, and Mass Spec (MS) analyses were done by Eli Lilly Physical Chemistry Laboratory. High pressure liquid chromatography conditions: Hitachi model L-6200A Intelligent Pump with D-2500 chromato-integrator. 25 cm Zorbax RX C-18 column, 60:40 $CH_3CN/H_2O$, 1.0 mL/minute, 275 nm, Injection –10 uL. Gas chromatography (GC) Conditions: HP 5890A GC with DB1 0.25 $\mu$×25 m column; 300° C. injection temperature; 300° C. detection (FID); column at 5° C. (5 minutes), 18 mL/minute to 250° C. then 250° C. for 20 minutes. The terms "NMR", "MS", "IR" and/or "GC" indicate that the product spectrum was analyzed and was consistent with the desired structure.

Preparation 1

6-bromo-2-tetralone propylene ketal.

1,3-bis-trimethylsilyloxy propandiol (38.5 grams, 175 mmol, prepared from 1,3-propanediol, triethylamine, and chlorotrimethyl silane in tetrahydrofuran) was slowly added to a stirring solution of trimethylsilyl trifluoromethanesulfonate (0.5 mL, 2.6 mmol) in methylene chloride (100 mL, –70° C.), while keeping the reaction temperature between –70° and –60° C. The solution was allowed to stir for 10 minutes at –70° C. A solution of 6-bromo-2-tetralone (35.5 grams, 158 mmol) in methylene chloride (100 mL) was slowly added over a 10 minute period. The resulting reaction mixture was allowed to warm slowly to 15° C. over 15 hours, after which time thin layer chromatography (55:45 diethyl ether:hexanes) and high pressure liquid chromatography showed complete consumption of the starting tetralone. The reaction was quenched with saturated sodium bicarbonate (200 mL) and the layers were separated. The aqueous layer was extracted with methylene chloride (50 mL). The combined methylene chloride solution was washed with brine (200 mL), dried with sodium sulfate, and concentrated at reduced pressure to a gold colored residue. This was filtered through 300 grams of silica gel and eluted with 3:1 hexanes/ethyl acetate. The filtrate was concentrated at reduced pressure and the product recrystallized from hexanes to obtain 33.5 grams (75% yield) of 6-bromo-2-tetralone propylene ketal as white crystals (NMR, MS). Calculated for $C_{13}H_{15}O_2Br$: C, 55.14; H, 5.34. Found C, 55.05; H, 5.52.

Preparation 2

6-methylthio-2-tetralone propylene ketal.

To a stirring solution of 6-bromo-2-tetralone propylene ketal (0.511 grams, 1.81 mmol) in tetrahydrofuran (5 mL, –75° C.), 2.5M n-butyllithium (0.76 mL, 1.90 mmol) was added dropwise while maintaining the temperature between –73° C. and –70° C. The resulting solution was allowed to stir at –70° C. for 15 minutes or until no more starting material was evident by thin layer chromatography (70:30 hexanes/ ethylacetate) upon quenching an aliquot of the reaction mixture with benzaldehyde. After 15 minutes, dimethyl disulfide (0.18 mL, 2.00 mmol) was added dropwise at −75° C. After stirring at −75° C. for 20 minutes, the reaction was diluted with ethyl acetate (25 mL) and quenched with saturated ammonium chloride (10 mL). The organic layer was separated, washed with brine (10 mL), dried over anhydrous sodium sulfate and concentrated at reduced pressure to a yellow oil. The crude product was purified by flash chromatography on silica gel (50 grams), eluted with 3:1 hexanes/ethyl acetate to obtain 0.39 grams (87%) of 6-methylthio-2-tetralone propylene ketal as a clear viscous oil (IR, NMR, MS). Calculated for $C_{14}H_{18}O_{2}S$: C, 67.17; H, 7.25. Found C, 67.04; H, 7.20.

Preparation 3
6-methylthio-2-tetralone.

A solution of 6-methylthio-2-tetralone propylene ketal (29.7 grams, 118 mmol) in tetrahydrofuran (50 mL) was treated with 6N hydrochloric acid (9 mL, 54 mmol) and stirred at room temperature for 3 hours or until thin layer chromatography (80:20 methylene chloride/hexanes) indicated complete consumption of the starting material. The reaction was diluted with ethyl acetate (60 mL) and saturated aqueous sodium bicarbonate (110 mL). The organic layer was separated. The aqueous layer was extracted with ethyl acetate (30 mL). The combined organic solution was shaken with brine (100 mL), dried with sodium sulfate, and concentrated at reduced pressure to an off-white solid. The crude product was purified by flash chromatography on silica gel (400 grams) and eluted with 5:1 hexanes/ethyl acetate to obtain 19.5 grams (85%) of 6-methylthio-2-tetralone as a white solid (IR, NMR, MS). Calculated for $C_{11}H_{12}OS$: C, 68.71; H, 6.29. Found C, 68.60; H, 6.31.

Preparation 4
6-methylthio-2-tetralone.

A solution of 4-methylthiophenylacetic acid (10 grams, 54.8 mmol) and dimethylformamide (0.1 grams, 1.37 mmol) in methylene chloride (50 mL) at 35° C. was treated with thionyl chloride (4.4 mL, 60.25 mmol). The solution was maintained at 35° C. for 30 minutes, after which the solvent was removed by distillation at reduced pressure and replaced with fresh methylene chloride (50 mL). The acid chloride solution and ethylene (4.6 grams, 164 mmol) were introduced simultaneously over 25 minutes to a stirred mixture of aluminum bromide (36.5 grams, 137 mmol) in methylene chloride (450 mL) at −15 to −10° C. The resulting reaction mixture was stirred for 2.5 hours at −10 to 0° C. Water (200 mL) was slowly added (temperature≦25° C.) and the layers separated. The organic layer was washed successively with 5% sodium bicarbonate (200 mL) and brine (200 mL), dried over sodium sulfate and concentrated at reduced pressure to yield a dark-colored oil. The oil was dissolved in 3A alcohol (12 mL) and treated with a solution of sodium bisulfite (22.8 grams) in water (40 ML) and 3A alcohol (12 mL). After 30 minutes at 20° C. and 1 hour at 0° C., the precipitated bisulfite addition complex was filtered, washed with cold 3A alcohol (15 mL) and then ether (50 mL). The filtered solid was added to a mixture of ether (100 mL) and potassium carbonate (22.7 grams, 164 mmol), dissolved in water (75 mL), and stirred vigorously at 22° C. until the solid was completely dissolved. The organic layer was separated, washed with 1N hydrochloric acid (100 mL), then water (200 mL), dried over sodium sulfate and concentrated at reduced pressure to yield 5.8 grams (48%) of 6-methylthio-2-tetralone as a beige solid (high pressure liquid chromatography purity: 88%).

Preparation 5
(+)-(4aR)-(10bR)-8-methylthio-10b-methyl-1.2,3,4,4a,5,6,10b-octahydrobenzo[f]quinolin-3-one.

A solution of 6-methylthio-2-tetralone (1 grams, 5.2 mmol, 1 equivalent) in dry toluene (18 mL) was treated with (R)-(+)-phenethylamine (0.72 ml, 5.7 mmol, 1.1 equivalent) and p-TsOH (6 mg). The solution was degassed 3 times with light vacuum/nitrogen and a positive nitrogen pressure was maintained. The solution was refluxed under Dean-Stark conditions to remove water. The progress of the imine formation was monitored by NMR. After 2.5 hours of refluxing, no starting ketone could be detected by $^1$H NMR. Toluene was distilled off with light vacuum and under nitrogen, being careful not to expose the mixture to air. Dry tetrahydrofuran (14 mL) was added to obtain a light purple solution which was kept at −70° C. under nitrogen. Lithium diisopropylamide was generated by dropwise addition of 2.5M hexanes solution of n-butyllithium (2.4 mL, 6.0 mmol, 1.15 equivalent) to a solution of diisopropylamine (0.78 mL, 6.0 mmol, 1.15 equivalent) in tetrahydrofuran (19 mL) at −45° C. under nitrogen. The temperature was kept between −45° C. and −30° C. during the addition. After the addition, the solution was stirred for 10 minutes at −45° C. Upon cooling the lithium diisopropylamide solution to −75° C., the imine solution was added dropwise over 15 minutes via cannula while maintaining the temperature between −70° C. and −75° C. The resulting yellowish-orange solution was allowed to warm to −20 C. over 20 minutes and then recooled to −75° C. Iodomethane (0.36 ml, 5.8 mmol, 1.15 equivalents) was added between −75° C. and −72° C. The solution was warmed (with the aid of an acetone bath) over 15 minutes to 0° C. Upon recooling to −5° C., methanesulfonic acid (0.43 mL, 6.6 mmol, 1.3 equivalents) was added over 2 minutes between −5° C. and 1° C. After 5 minutes at 0° C., a gray heterogeneous mixture resulted. The mixture was recooled to −75° C. A 1.125M tetrahydrofuran solution of acrylic anhydride (11 mL, 12.5 mmol, 2.4 equivalents) was added quickly. The mixture was kept in the cooling bath for 15 hours, during which time it warmed to 13° C. The reaction was allowed to warm to 15° C. Water (2 mL) was added and the mixture stirred while warming the mixture to room temperature. The solution was diluted with diethyl ether (50 mL) and washed successively with 1N sodium hydroxide (20 mL), 1N hydrochloric acid (20 mL), water (20 mL), saturated aqueous sodium bicarbonate (40 mL), and brine (20 mL). The sodium sulfate solution was dried, concentrated and was flash chromatographed on silica gel (120 grams), eluting with 70:30 hexanes/ethyl acetate) to obtain 1.3 grams (69% yield) of (+)-(10bR)-4-(2-(R)-phenethyl)-8-methylthio-10b-methyl-1,2,3,4,6,10b-hexahydrobenzo[f]quinolin-3-one (NMR). A mixture of triethylsilane (12 mL, 75 mmol) and trifluoroacetic acid (14.5 mL, 188 mmol) precooled to −15° C. under nitrogen was added to (+)-(10bR)-4-(2-(R)-phenethyl)-8-methylthio-10b-methyl-1,2,3,4,6,10b-hexahydrobenzo[f]quinolin-3-one (2.76 grams, 7.6 mmol) precooled in −15° C. bath. The mixture was stirred for 15 hours, during which time it warmed to 13° C. Thin layer chromatography (70:30 hexanes/ethyl acetate) and high pressure liquid chromatography showed complete disappearance of (+)-(10bR)-4-(2-(R)-phenethyl)-8-methylthio-10b-methyl-1,2,3,4,6,10b-hexahydrobenzo[f]quinolin-3-one and the appearance of a new product, indicating complete double bond reduction. The mixture was then refluxed for 2 hours to remove the chiral auxiliary. Upon cooling to room temperature, the mixture was concentrated at reduced pressure. The residue was taken up in methylene chloride (50 mL) and washed twice with saturated aqueous sodium bicarbonate (35 mL) and brine (50 mL). The dried sodium sulfate and concentrated crude product was purified by flash chromatography on silica gel (100 grams), eluting first with 3:1 hexanes/ethyl acetate to remove triethylsilane and then with 14% methanol in methylene chloride with 1% acetic acid to obtain a foamy solid. Recrystallization from hot ethyl acetate gave 1.6 grams (82%) of (+)-(4aR)-(10bR)-8-methylthio-10b-methyl-1,2,3,4,4a,5,6,10b-octahydrobenzo[f]quinolin-3-one (92% ee, IR, NMR, MS). Calculated for $C_{15}H_{19}NOS$: C, 68.93; H, 7.33. Found C, 69.05; H, 7.44.

Preparation 6

(+)-(4aR)-(10bR)-4-methyl-8-methylthio-10b-methyl-1,2,3,4,4a,5,6,10b-octahydrobenzo[f]quinolin-3-one.

(+)-(4aR)-(10bR)-8-methylthio-10b-methyl-1,2,3,4,4a,5,6,10b-octahydrobenzo[f]quinolin-3-one (0.423 grams, 1.62 mmol, 1.0 equivalents) was treated with potassium t-butoxide (1.86 mL as a 1.0 M solution in tetrahydrofuran, 1.15 equivalents) in dimethylformamide (1.6 mL) at approximately 0° C. After stirring 5 minutes, methyl iodide (0.116 mL, 1.15 equivalents) was added and the mixture allowed to stir for 2 hours at 0° C. The mixture was then treated with approximately 100 mg of acetic acid and solvents were removed in a stream of nitrogen. The solid was dissolved in approximately 50 mL of methylene chloride and washed twice with water. The extracts were dried (4 molecular sieves) and filtered over silica gel (2 grams, washed with ethyl acetate containing 2% methanol). The solid from the evaporation of the methylene chloride extracts was chromatographed on silica gel with methylene chloride, ethyl acetate and methanol (50:50:1) as the eluent. (GC).

Preparation 7

(+)-(4aR)-(10bR)-4-methyl-8-methylthio-10b-methyl-1,2,3,4,4a,5,6,10b-octahydrobenzo[f]quinolin-3-one.

(+)-(4aR)-(10bR)-4-methyl-8-bromo-10b-methyl-1,2,3,4,4a,5,6,10b-octahydrobenzo[f]quinolin-3-one (20.0 grams, 64.9 mmole, in 150 mL of tetrahydrofuran) was added to a freshly prepared solution of lithium diisopropylamide in 500 mL of tetrahydrofuran at −20° C. After standing 90 minutes in an ice bath, the resulting amide-enolate solution was cooled to −70° C. and added via cannula over 10 minutes to a freshly mixed solution of n-butyllithium (60.0 mL=2.54 M in hexane, 152 mmole, 2.34 equivalents) at −72 to −75° C. in 300 mL of tetrahydrofuran. The homogeneous solution was allowed to stir at approximately −75° C. for 45 minutes and quenched with dimethyldisulfide (11.0 mL, 123 mmole, 1.9 equiv) at approximately −75° C. After 30 minutes at −75° C., the mixture was treated with acetic acid (18 mL) and all volatiles removed under vacuum. The resulting white solid was treated with 300 mL of heptane-water (1:1, v/v) and the pH adjusted to 3 with 1N hydrogen sulfate. The biphasic mixture was filtered and the wet cake was washed with 1% aqueous sodium bicarbonate (2×50 mL portion) and water (200 mL). The material was dried at 50° C. under vacuum affording (+)-(4aR)-(10bR)-4-methyl-8-methylthio-10b-methyl-1,2,3,4,4a,5,6,10b-octahydrobenzo[f]quinolin-3-one (IR, NMR, MS). Calculated for $C_{16}H_{21}NOS$: C, 69.77; H, 7.69; N, 5.09. Found C, 69.70; H, 7.62; N, 5.06.

Preparation 8

(+)-(4aR)-(10bR)-4-methyl-8-methylthio-10b-methyl-1,2,3,4,4a,5,6,10b-octahydrobenzo[f]quinolin-3-one.

Lithium chloride (1.80 grams, 2.46 mmole; 10 equivalents) was rapidly weighed and placed in a 500 ml flask equipped with mechanical stirring, pressure equalizing addition funnel, thermocouple, injection septum and nitrogen inlet. (+)-(4aR)-(10bR)-4-Methyl-8-bromo-10b-methyl-1,2,3,4,4a,5,6,10b-octahydrobenzo[f]quinolin-3-one (13.09 grams, 2.46 mmole; 1.0 equivalents) and 100 mL of dry tetrahydrofuran were added and stirred until dissolved (10–15 minutes.). Then, 46.71 mL of lithium hexamethyldisilazide (LiN(TMS)2, 46.71 mmole; 1.1 equivalents) in tetrahydrofuran was added via syringe over 40 minutes (1 degree exotherm). A clear yellow solution resulted and was stirred at room temperature for 1 hour. Methyllithium (1.4M in diethyl ether; 33.36 mL; 46.71 mmole; 1.1 equivalents) was added dropwise via syringe over 50 minutes. Gas evolution was observed and the reaction was exothermic from 23 to 26 degrees. The exothermic reaction was controlled using standard procedures. The reaction mixture was allowed to stir at room temperature for 45 minutes and was then cooled to −70° C. n-butyllithium (1.6M in hexane; 29.2 mL; 46.71 mmole; 1.1 equivalents) was added via syringe over 25 minutes while the reaction temperature was maintained at −71/−70° C. The remaining yellow solution was maintained at −70° C. and stirred for 35 minutes. High pressure liquid chromatography showed nearly complete dianion formation after 15 minutes. Dimethyldisulfide (4.00 grams; 42.46 mmole; 1.0 equivalents) was dissolved in 25 mL of tetrahydrofuran and added over 50 minutes. The mixture was stirred for 30 minutes (−70° C.). High pressure liquid chromatography showed the reaction was complete after 10 minutes. The mixture was quenched with 1N hydrochloric acid (100 mL, −70° C). The reaction was warmed to room temperature and the aqueous layer was extracted with 200 mL of methyl t-butyl ether. The organic layers were combined and washed with 50 mL. of brine. The organic layers were dried over magnesium sulfate and filtered and concentrated on rotovap™@35° C. and house-vac. A white solid formed as the volume decreased. The organics were concentrated from 550 mL to approximately 30–40 mL. of a white slurry. The slurry was stirred at room temperature for a few hours followed by filtration with small portions of methyl t-butyl ether until the washes were colorless. The white solid was dried and afforded 7.73 grams (66%) of (+)-(4aR)-(10bR)-4-methyl-8-methylthio-10b-methyl-1,2,3,4,4a,5,6,10b-octahydrobenzo[f]quinolin-3-one.

Preparation 9

(+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

A solution of meta-chloroperoxybenzoic acid (approximately 56% potency, 6.32 grams as a solution in methylene chloride) was added to a mixture of (+)-(4aR)-(10bR)-4-methyl-8-methylthio-10b-methyl-1,2,3,4,4a,5,6,10b-octahydrobenzo[f]quinolin-3-one. (5.50 grams in 110 mL of methylene chloride) and aqueous sodium bicarbonate (9.4 grams in 110 mL of water) at 0 to −1° C. over approximately one hour. After 8 hours, the layers were separated and the organic extracts were washed twice with aqueous 1% sodium bicarbonate, dried (4A molecular sieves) and evaporated to a total weight of 5.90 grams. A portion (2.91 grams) of this non-purified sulfoxide in 10 mL of toluene-$d_8$ was treated with 2.20 mL of trifluoroacetic anhydride at 5–10° C. After 30 minutes., 1H NMR analysis of a 0.50 mL aliquot showed none of the starting sulfoxide (ArSOCH$_3$ singlet absent at d=2.25 ppm) and the exclusive formation of the Pummerer product (ArSCH$_2$OCOCF$_3$, singlet at d=5.31 ppm). The reaction mixture was subjected to vacuum (5–10 torr) for 30 minutes after which the contents were added to a stirred mixture (under nitrogen) of water (20 mL), tetra-n-butylammonium hydrogen sulfate (0.1 gram), and 7.1 mL of water soluble borohydride (12% by weight of sodium borohydride in 14 N sodium hydroxide) at 5–10° C. over 20 minutes. After an additional 20 minutes, 2-chloro-4-ethylbenzothiazole (3.00 grams with an additional 9.5 mL of toluene-$d_8$) and another portion of tetra-n-butylammonium hydrogen sulfate (0.50 gram) were added. The reaction was stirred at 37–39° C. during which, four 0.25-mL portions were removed for direct $^1$H NMR assay and high pressure liquid chromatography for analysis of the conversion and product distribution. After 26 hours the top-most layer (toluene containing (+)-(4aR)-(10bR)-4-methyl-8-(4-ethyl-2-benzothiazolylthio)-10b-methyl-1,2,3,4,4a,5,6,10b-octahydrobenzo[f]quinolin-3-one and excess 2-chloro-4-ethylbenzothiazole) of the three phase mixture was separated and diluted with 25 mL of methylene chloride. This organic layer was washed with aqueous 1 N sulfuric acid, aqueous 5% sodium bicarbonate, dried with 4 Å molecular sieves, and concentrated under vacuum to 5.24 grams. The resulting solid was digested with hot methyl t-butyl ether (30 mL) after which it was concentrated under vacuum to 20 mL and then cooled to 0° C. The mixture was filtered and the white solid was dried affording 2.92 grams of (+)-(4aR)-(10bR)-4-methyl-8-(4-ethyl-2-benzothiazolylthio)-10b-methyl-1,2,3,4,4a,5,6,10b-octahydrobenzo[f]quinolin-3-one (IR, NMR, MS). Calculated for $C_{24}H_{26}N_2OS_2$: C, 67.93; H, 6.16; N, 6.83; S, 15.08. Found C, 68.21; H, 6.20; N, 6.63; S, 15.17.

Preparation 10

(+)-(4aR)-(10bR)-4-methyl-8-(4-ethyl-2-benzothiazolylthio)-10b-methyl-1,2,3,4,4a,5,6,10b-octahydrobenzo[f]quinolin-3-one. A solution of meta-chloroperoxybenzoic acid (35.2 mmole in 100 mL of methylene chloride) was added to. (+)-(4aR)-(10bR)-methyl-8-methylthio-10b-methyl-1,2,3,4,4a,5,6,10b-octahydrobenzo[f]quinolin-3-one (10.0 grams, 98% purity by weighted standard potency assay, 35.6 mmoles) in a biphasic mixture of methylene chloride (200 mL) and aqueous sodium bicarbonate (8.90 grams in 89 mL water) at -2 to 0° C. over a period of 1 hour. The layers were separated and the methylene chloride layers washed once with sodium metabisulfite (1.00 gram in 25 mL) and three times with sodium bicarbonate (1.00 gram in 100 mL). The dried (4 A molecular sieves) methylene chloride extract was concentrated to approximately 20 mL and diluted with 100 mL of toluene. The mixture was then concentrated under vacuum at 30–35° C. This process was repeated twice with fresh toluene (100 mL portions each) after which the sulfoxide (usually crystalline) was diluted with toluene (100 mL). The mixture was then treated with trifluoroacetic anhydride (7.30 mL) over 10 minutes at 0 to 10° C. After 30 minutes at 0° C., this solution was subjected to vacuum (<10 torr) for 30 minutes and added over 30 minutes to a degassed (nitrogen) mixture of potassium carbonate (41 grams), sodium borohydride (2.88 grams), tetra-n-butylammonium hydrogen sulfate (2.00 grams), and 2-chloro-4-ethylbenzothiazole (8.20 grams at 96.5% purity dissolved in 5 mL of toluene) and water (87 mL) at 0–5° C. This mixture was warmed to 40° C. over one hour and then stirred at 40° C. for 26 hours. The toluene layer was separated (while warm) and washed with 3×100-mL portions of water. The toluene layer was diluted with 125 mL ethyl acetate and then washed in sequence with 3×200 mL portions of 0.25 N hydrochloric acid, 100 mL of 1% sodium bicarbonate and the 100 mL of saturated aqueous sodium chloride. The organic layer was dried (10 grams of 4 Å molecular sieves), concentrated to a total volume of 25 mL and treated with 100 mL of methyl t-butyl ether (refluxed for 30 minutes then, 0° C. for 1 hour) affording (+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

Preparation 11

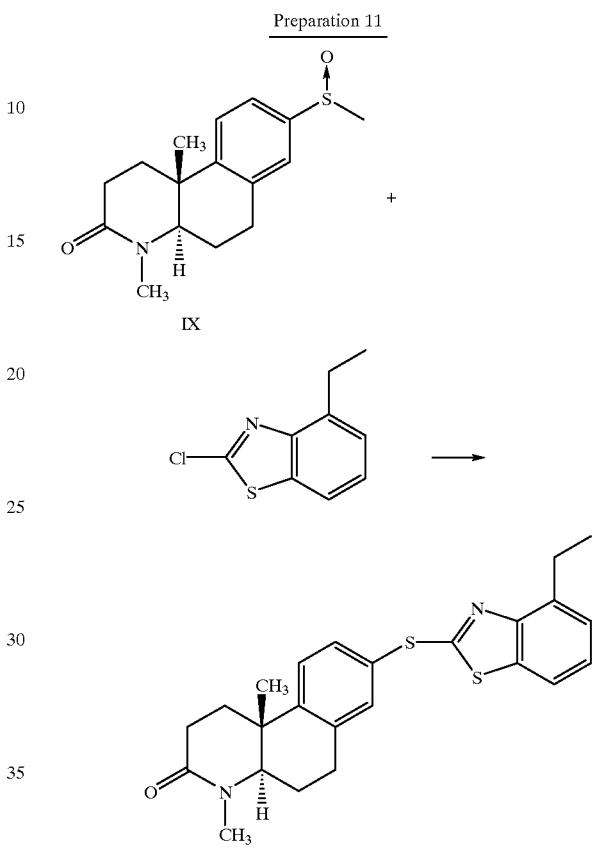

Preparation 11

(+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

The dry sulfoxide IX (96% purity by gas chromatography, 8.90 grams, 29.4 mmol corrected) as a suspension in toluene (89 mL) was treated dropwise with trifluoroacetic anhydride (5.2 mL) at 0–5° C. in 20 minutes (dissolution occurs). After 30 minutes, the solution was added to a mixture of potassium carbonate (32 grams), water (45 mL), tetrabutylammonium hydrogen sulfate (2.25 grams), sodium borohydride (1.0 grams), the 2-chloro-4-ethylbenzothiazole (7.07 grams, approximately 96.5 % purity by gas chromatography), and toluene (10 mL) at approximately 5–15° C. over 30 minutes. The biphasic mixture was then stirred for 20 hours at 43° C. after which a small amount of solid was filtered from the reaction mixture. The warm toluene layer was washed once with 400 mL of water (45°0 C.) and then evaporated under vacuum yielding 13.86 grams of white solid consisting of mainly (+)-(4aR)-(10bR)-4-methyl-8-(4-ethyl-2-benzothiazolylthio)-10b-methyl-1,2,3,4,4a,5,6,10b-octahydrobenzo[f]quinolin-3-one and 2-chloro-4-ethylbenzothiazole. 13.0 grams of this mixture was treated with methyl t-butyl ether (50 mL at reflux then 0° C. for 2 hours) affording 11.05 grams of (+)-(4aR)-(10bR)-4-methyl-8-(4-ethyl-2-benzothiazolylthio)-10b-methyl-1,2,3,4,4a,5,6,10b-octahydrobenzo[f]quinolin-3-one (IR, NMR, MS). Calculated for C, 68.21; H, 6.20; N, 6.63. Found C, 68.29; H, 6.15; N, 6.67.

Preparation 12

(+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

meta-Chloroperoxybenzoic acid (approximately 92 grams, approximately 50% potency, in 1.0 L of methylene chloride) was added at 0° C. to a solution of (+)-(4aR)-(10bR)-4-methyl-8-methylthio-10b-methyl-1,2,3,4,4a,5,6,10b-octahydrobenzo[f] quinolin-3-one (79.5 grams, 92.9% potency, 0.269 moles) in methylene chloride (2.2 L). The progress of the reaction was monitored by high pressure liquid chromatography (240 rim) for the oxidation of (+)-(4aR)-(10bR)-4-methyl-8-methylthio-10b-methyl-1,2,3,4,4a,5,6,10b-octahydrobenzo[f]quinolin-3-one to a level of less than 0.3% by area. The organic solution was stirred with a sodium bisulfite solution (75 grams in 1 L deionized water). The organic layer was separated, and washed with 6% sodium bicarbonate solution (3×1 L). The organic layer was dried over sodium sulfate and concentrated. Toluene (1 L) was added to the intermediate sulfoxide and this solution was concentrated under vacuum. This was repeated twice with fresh toluene (1.1 L each) after which the sulfoxide was dissolved in 1.1 L of toluene and cooled in an ice bath. Trifluoroacetic anhydride (51 mL) was added dropwise to the sulfoxide at 0° C. over 15 minutes. After 30 minutes of stirring at 0° C., the Pummerer product (ArSCH$_2$OCOCF$_3$) was added via cannula to a well stirred mixture of deionized water (414 mL), potassium carbonate (319 grams), sodium borohydride (15.2 grams), 2-chloro-4-ethylbenzothiazole (65.7 grams approximately 96.5% purity), tetrabutylammonium hydrogen sulfate (21.6 grams), and toluene (170 mL) at 10° C. The reaction was heated slowly to 42° C. while monitoring the progress by high pressure liquid chromatography. After 18 hours, an additional volume of toluene (1.0 L) was added and the toluene layers washed with deionized water (3×1 L, 45° C.). To the organic layer was added ethyl acetate (1 L) then the organic layer washed with 0.25 M hydrochloric acid solution (3×1 L), iN sulfuric acid solution (3×1 L), 6% sodium bicarbonate solution (1.5 L), and saturated sodium chloride solution (2 L). The organic extracts were dried over 4 Å molecular sieves (500 grams) then concentrated. Methyl t-butyl ether was added (400 mL) and the mixture heated to reflux. After 30 minutes of stirring at reflux the mixture was cooled to 5° C. The suspension was filtered and washed with methyl t-butyl ether (100 mL). The solution was filtered and the product was dried at 50° C. at approximately 5 mm for 18 hours affording 90.1 grams (80%) of (+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

We claim:

1. A process for preparing a compound of the formula I

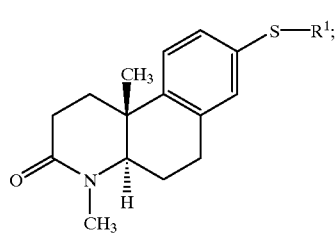

wherein R$^1$ represents:
2-nitrophenyl, 4-nitrophenyl, 2-cyanophenyl, 4-cyanophenyl, 2-nitronaphthyl, 4-nitronaphthyl, 2-cyanonaphthyl, 4-cyanonaphthyl, 2-quinolinyl, 4-quinolinyl, 7-quinolinyl, 1-isoquinolinyl, 3-isoquinolinyl, 8-isoquinolinyl, 2-quinoxalinyl, 2-benzothiazolyl, 3-1H-indazolyl, 2-benzoxazolyl, 3-1,2-benzisothiazolyl, 2-pyridinyl, 4-pyridinyl, 2-pyrazinyl, 2-naphtho[2,3-d]thiazolyl, 2-naphtho[1,2-d]thiazolyl, 9-anthryl, 2-thiazolyl, 2-benzimidazolyl, 1-benz[g]isoquinolinyl, 8-benz[g]isoquinolinyl, 5-1H-tetrazolyl, 2-quinazolinyl, 2-thiazolo[4,5-b]pyridinyl, 4-10H-pyridazino[3,2-b]-2-quinazolinyl, 2-1,4-benzodioxinyl, 2-triazine, 2-benzoxazine, 4-benzoxazine, 2-purine or 8-purine;

wherein the above R$^1$ groups are unsubstituted or substituted with 1–3 groups chosen from the group consisting of trifluoromethyl, trifluoroethoxy, C$_1$–C$_4$ alkyl, trifluoromethoxy, hydroxy, C$_1$–C$_3$ alkoxy, nitro, C$_1$–C$_3$ alkylthio, C$_1$–C$_6$ alkanoyl, phenyl, oxo, phenoxy, phenylthio, C$_1$–C$_3$ alkylsulfinyl, C$_1$–C$_3$ alkylsulfonyl, cyano, amino, C$_1$–C$_3$ alkylamino, diphenylmethylamino, triphenylmethylamino, benzyloxy, benzylthio, (mono-halo, nitro or CF$_3$) benzyl(oxy or thio), di(C$_1$–C$_3$ alkyl, C$_3$–C$_6$ cycloalkyl, or C$_4$–C$_8$ cycloalkylalkyl)amino, (mono-C$_1$–C$_3$ alkyl, C$_1$–C$_3$ alkoxy or halo)(phenyl, phenoxy, phenylthio, phenylsulfonyl or phenoxysulfonyl), C$_2$–C$_6$ alkanoylamino, benzoylamino, diphenylmethylamino (C$_1$–C$_3$ alkyl), aminocarbonyl, C$_1$–C$_3$ alkylaminocarbonyl, di(C$_1$–C$_3$ alkyl)aminocarbonyl, halo-C$_1$–C$_6$ alkanoyl, aminosulfonyl, C$_1$–C$_3$ alkylaminosulfonyl, di(C$_1$–C$_3$ alkyl)aminosulfonyl, phenyl(oxy or thio)(C$_1$–C$_3$ alkyl), (halo, C$_1$–C$_3$ alkyl or C$_1$–C$_3$ alkoxy)phenyl(oxy or thio)(C$_1$–C$_3$ alkyl), benzoyl, or (amino, C$_1$–C$_3$ alkylamino or di(C$_1$–C$_3$ alkyl)amino)(C$_1$–C$_3$ alkyl);

which comprises: converting a ketone of the formula

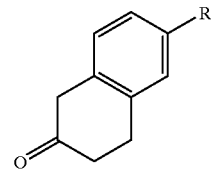

wherein R is halogen;

to a protected ketal;

reacting the protected ketal with a reactive alkyllithium compound and a sulfur transfer reagent to afford an S-methylated ketal compound;

deprotecting the S-methylated ketal compound to afford a methyl-thiotetralone compound of the formula II

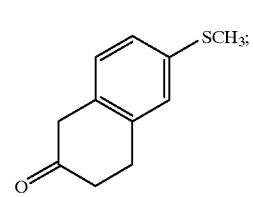

reacting the compound of formula II with (R)-(+)-phenethylamine to afford a compound of the formula III

III

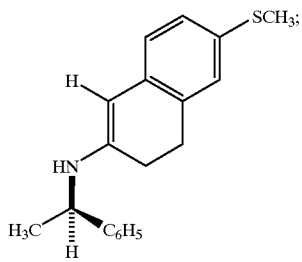

reacting the compound of formula III with a strong lithium base to afford a lithioenamine compound of the formula IV

IV

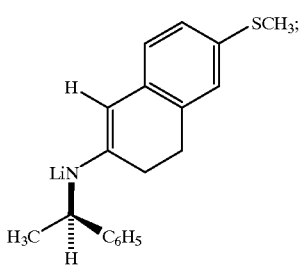

methylating the resulting lithioenamine of the formula IV to a compound of the formula V

V

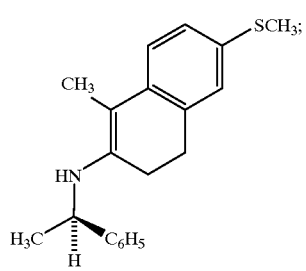

reacting the compound of formula V with an acyl halide or an anhydride of acrylic acid to prepare a compound of the formula VI

VI

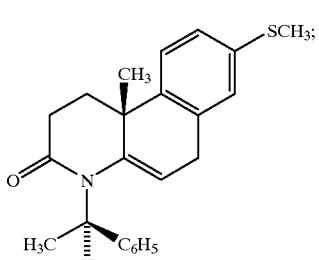

quenching the reaction with base, and combining the residue comprising the compound of formula VI with an appropriate silane and trifluoroacetic acid in the absence of a solvent to prepare a compound of the formula VII

VII

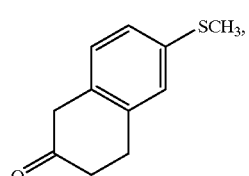

reacting the compound of formula VII with a methyl halide in a reaction mixture comprising an organic solvent and a strong base to afford an arylmethylsulfide compound of the formula VIII

VIII

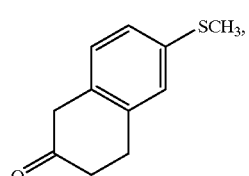

oxidizing the compound of formula VIII to a sulfoxide compound of the formula IX

IX

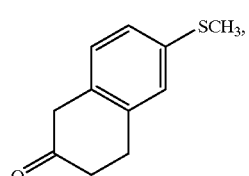

reacting the sulfoxide compound of the formula IX with an acylating agent to afford a Pummerer rearrangement product;

reacting the Pummerer rearrangement product with an electrophile selected from the group consisting of A-R$^1$ wherein A is a leaving group, in the presence of a phase transfer catalyst, a hydride reducing reagent and a base, to prepare a compound of the formula I.

2. A process for preparing the compound of formula II

II

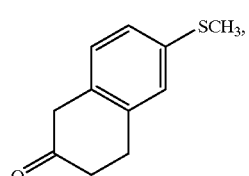

which comprises: converting a ketone of the formula

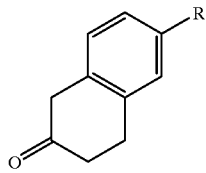

wherein R is halogen;
to a protected ketal;
reacting the protected ketal with a reactive alkyllithium compound and a sulfur transfer reagent to afford an S-methylated ketal compound; deprotecting the S-methylated ketal compound to afford the methylthiotetralone compound of the formula II.

3. The process of claim 2, wherein the sulfur transfer reagent is dimethyl disulfide and the protected ketal is

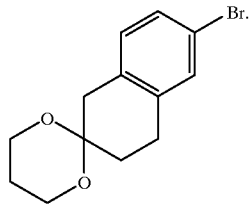

4. A process for preparing a compound of the formula II

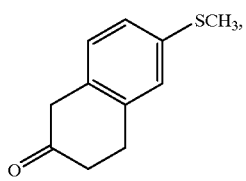

which comprises: reacting a compound of the formula

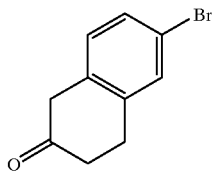

with lithium diisopropylamide, n-butyllithium and dimethyl disulfide.

5. A process for preparing the compound of formula II

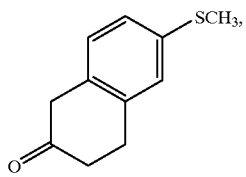

which comprises: converting a compound of the formula XI

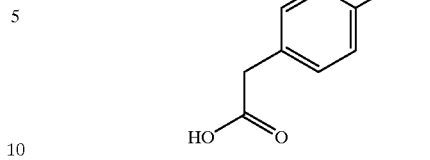

to an acid halide;
reacting the acid halide with a Lewis acid and ethylene to afford the compound of formula II.

6. The process of claim 5, wherein methylene chloride, thionyl chloride and a catalytic amount of dimethylformamide are employed to afford the acid halide and aluminum bromide is employed as the Lewis acid.

7. The process of any one of claims 2, 3, 4, 5 or 6, further comprising converting the compound of formula II

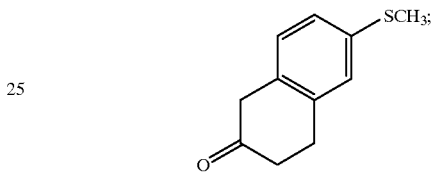

to a compound of the formula I

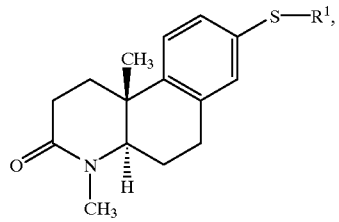

wherein R represents:
2-nitrophenyl, 4-nitrophenyl, 2-cyanophenyl, 4-cyanophenyl, 2-nitronaphthyl, 4-nitronaphthyl, 2-cyanonaphthyl, 4-cyanonaphthyl, 2-quinolinyl, 4-quinolinyl, 7-quinolinyl, 1-isoquinolinyl, 3-isoquinolinyl, 8-isoquinolinyl, 2-quinoxalinyl, 2-benzothiazolyl, 3-1H-indazolyl, 2-benzoxazolyl, 3-1,2-benzisothiazolyl, 2-pyridinyl, 4-pyridinyl, 2-pyrazinyl, 2-naphtho[2,3-d]thiazolyl, 2-naphtho[1,2-d]thiazolyl, 9-anthryl, 2-thiazolyl, 2-benzimidazolyl, 1-benz[g]isoquinolinyl, 8-benz[g]isoquinolinyl, 5-1H-tetrazolyl, 2-quinazolinyl, 2-thiazolo[4,5-b]pyridinyl, 4-10H-pyridazino[3,2-b]-2-quinazolinyl, 2-1,4-benzodioxinyl, 2-triazine, 2-benzoxazine, 4-benzoxazine, 2-purine or 8-purine;
wherein the above $R^1$ groups are unsubstituted or substituted with 1–3 groups chosen from the group consisting of trifluoromethyl, trifluoroethoxy, $C_1$–$C_4$ alkyl, trifluoromethoxy, hydroxy, $C_1$–$C_3$ alkoxy, nitro, $C_1$–$C_3$ alkylthio, C1-C6 alkanoyl, phenyl, oxo, phenoxy, phenylthio, $C_1$–$C_3$ alkylsulfinyl, $C_1$–$C_3$ alkylsulfonyl, cyano, amino, $C_1$–$C_3$ alkylamino, diphenylmethylamino, triphenylmethylamino, benzyloxy, benzylthio, (mono-halo, nitro or $CF_3$) benzyl(oxy or thio), di($C_1$–$C_3$ alkyl, $C_3$–$C_6$ cycloalkyl, or $C_4$–$C_8$ cycloalkylalkyl)amino, (mono-$C_1$–$C_3$ alkyl, $C_1$–$C_3$ alkoxy or halo)(phenyl, phenoxy, phenylthio, phenylsulfonyl or phenoxysulfonyl), $C_2$–$C_6$ alkanoylamino, benzoylamino, diphenylmethylamino ($C_1$–$C_3$ alkyl), minocarbonyl, $C_1$–$C_3$ alkylaminocarbonyl, di($C_1$–$C_3$ alkyl)aminocarbonyl, halo-$C_1$–$C_6$ alkanoyl, aminosulfonyl, $C_1$–$C_3$ alkylaminosulfonyl, di($C_1$–$C_3$ alkyl)aminosulfonyl, phenyl(oxy or thio)($C_1$–$C_3$ alkyl), (halo, $C_1$–$C_3$ alkyl or $C_1$–$C_3$ alkoxy)phenyl(oxy or thio) ($C_1$–$C_3$ alkyl), benzoyl, or (amino, $C_1$–$C_3$ alkylamino or di($C_1$–$C_3$ alkyl)amino)($C_1$–$C_3$ alkyl).

8. The process of any one of claims 2, 3, 4, 5 or 6, further comprising converting the compound of the formula II

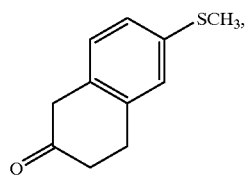

II to (+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

9. The process as in any one of claims 2, 3, 4, 5, or 6, further comprising: reacting the compound of the formula II

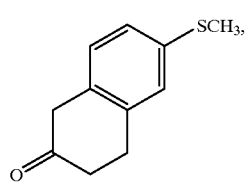

II with (R)-(+)- phenethylamine to afford a compound of the formula III

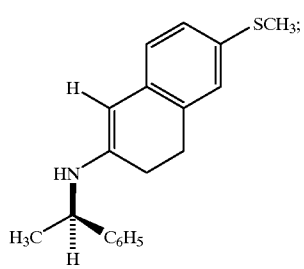

III reacting the compound of formula III with a strong lithium base to afford a lithioenamine compound of the formula IV

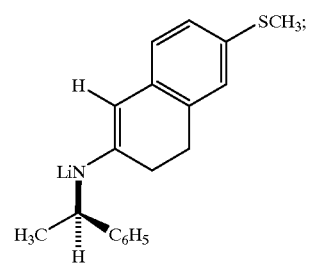

IV methylating the resulting lithioenamine of the formula IV to a compound of the formula V

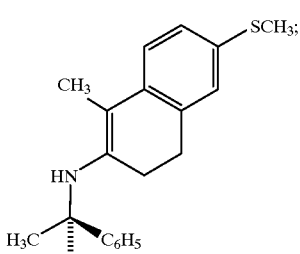

V reacting the compound of formula V with an acyl halide or an anhydride of acrylic acid to prepare a compound of the formula VI

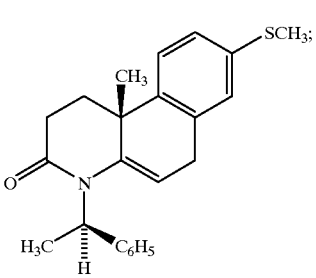

VI quenching the reaction with base, and combining the residue comprising the compound of formula VI with an appropriate silane and trifluoroacetic acid in the absence of a solvent to prepare a compound of the formula VII

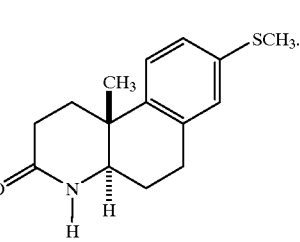

VII

10. The process of claim 9, further comprising: reacting the compound of formula VII with a methyl halide in a reaction mixture comprising an organic solvent and a strong base to afford an arylmethylsulfide compound of the formula VIII

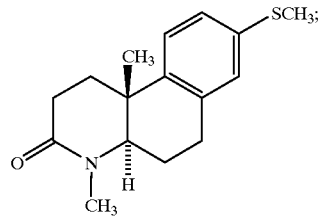

VIII oxidizing the compound of formula VIII to a sulfoxide compound of the formula IX

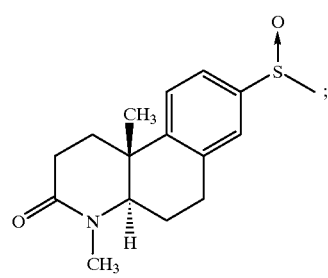

IX reacting the sulfoxide compound of the formula IX with an acylating agent to afford a Pummerer rearrangement product;

reacting the Pummerer rearrangement product with an electrophile selected from the group consisting of A-R$^1$ wherein A leaving group and R$^1$ represents:

2-nitrophenyl, 4-nitrophenyl, 2-cyanophenyl, 4-cyanophenyl, 2-nitronaphthyl, 4-nitronaphthyl, 2-cyanonaphthyl, 4-cyanonaphthyl, 2-quinolinyl, 4-quinolinyl, 7-quinolinyl, 1-isoquinolinyl, 3-isoquinolinyl, 8-isoquinolinyl, 2-quinoxalinyl, 2-benzothiazolyl, 3-1H-indazolyl, 2-benzoxazolyl, 3-1,2-benzisothiazolyl, 2-pyridinyl, 4-pyridinyl, 2-pyrazinyl, 2-naphtho[2,3-d]thiazolyl, 2-naphtho[1,2-d]thiazolyl, 9-anthryl, 2-thiazolyl, 2-benzimidazolyl, 1-benz[g]isoquinolinyl, 8-benz[g]isoquinolinyl, 5-1H-tetrazolyl, 2-quinazolinyl, 2-thiazolo[4,5-b]pyridinyl, 4-10H-pyridazino[3,2-b]-2-guinazolinyl, 2-1,4-benzodioxinyl, 2-triazine, 2-benzoxazine, 4-benzoxazine, 2-purine or 8-purine;

wherein the above R$^1$ groups are unsubstituted or substituted with 1–3 groups chosen from the group consisting of trifluoromethyl, trifluoroethoxy, C$_1$–C$_4$ alkyl, trifluoromethoxy, hydroxy, C$_1$–C$_3$ alkoxy, nitro, C$_1$–C$_3$ alkylthio, C$_1$–C$_6$ alkanoyl, phenyl, oxo, phenoxy, phenylthio, C$_1$–C$_3$ alkylsulfinyl, C$_1$–C$_3$ alkylsulfonyl, cyano, amino, C$_1$–C$_3$ alkylamino, diphenylmethylamino, triphenylmethylamino, benzyloxy, benzylthio, (mono-halo, nitro or CF$_3$) benzyl(oxy or thio), di(C$_1$–C$_3$ alkyl, C$_3$–C$_6$ cycloalkyl, or C$_4$–C$_8$ cycloalkylalkyl)amino, (mono-C$_1$–C$_3$ alkyl, C$_1$–C$_3$ alkoxy or halo)(phenyl, phenoxy, phenylthio, phenylsulfonyl or phenoxysulfonyl), C$_2$–C$_6$ alkanoylamino, benzoylamino, diphenylmethylamino (C$_1$–C$_3$ alkyl), aminocarbonyl, C$_1$–C$_3$ alkylaminocarbonyl, di(C$_{h1}$–C$_3$ alkyl)aminocarbonyl, halo-C$_1$–C$_6$ alkanoyl, aminosulfonyl, C$_1$–C$_3$ alkylaminosulfonyl, di(C$_1$–C$_3$ alkyl)aminosulfonyl, phenyl(oxy or thio)(C$_1$–C$_3$ alkyl), (halo, C$_1$–C$_3$ alkyl or C$_1$–C$_3$ alkoxy)phenyl(oxy or thio)(C$_1$–C$_3$ alkyl), benzoyl, or (amino, C$_1$–C$_3$ alkylamino or di(C$_1$–C$_3$ alkyl)amino)(C$_1$–C$_3$ alkyl);

in the presence of a phase transfer catalyst, a hydride reducing reagent and a base, to prepare a compound of formula I

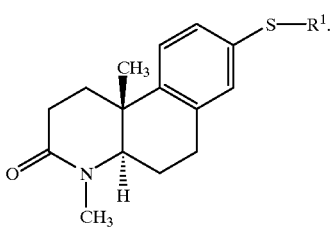

I

11. A process for preparing a compound of the formula

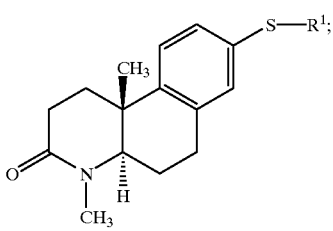

I wherein R$^1$ represents:

2-nitrophenyl, 4-nitrophenyl, 2-cyanophenyl, 4-cyanophenyl, 2-nitronaphthyl, 4-nitronaphthyl, 2-cyanonaphthyl, 4-cyanonaphthyl, 2-quinolinyl, 4-quinolinyl, 7-quinolinyl, 1-isoquinolinyl, 3-isoquinolinyl, 8-isoquinolinyl, 2-quinoxalinyl, 2-benzothiazolyl, 3-1H-indazolyl, 2-benzoxazolyl, 3-1,2-benzisothiazolyl, 2-pyridinyl, 4-pyridinyl, 2-pyrazinyl, 2-naphtho[2,3-d]thiazolyl, 2-naphtho[1,2-d]thiazolyl, 9-anthryl, 2-thiazolyl, 2-benzimidazolyl, 1-benz[g]isoquinolinyl, 8-benz[g]isoquinolinyl, 5-1H-tetrazolyl, 2-quinazolinyl, 2-thiazolo[4,5-b]pyridinyl, 4-10H-pyridazino[3,2-b]-2-quinazolinyl, 2-1,4-benzodioxinyl, 2-triazine, 2-benzoxazine, 4-benzoxazine, 2-purine or 8-purine;

wherein the above R$^1$ groups are unsubstituted or substituted with 1–3 groups chosen from the group consisting of trifluoromethyl, trifluoroethoxy, C$_1$–C$_4$ alkyl, trifluoromethoxy, hydroxy, C$_1$–C$_3$ alkoxy, nitro, C$_1$–C$_3$ alkylthio, C$_1$–C$_6$ alkanoyl, phenyl, oxo, phenoxy, phenylthio, C$_1$–C$_3$ alkylsulfinyl, C$_1$–C$_3$ alkylsulfonyl, cyano, amino, C$_1$–C$_3$ alkylamino, diphenylmethylamino, triphenylmethylamino, benzyloxy, benzylthio, (mono-halo, nitro or CF$_3$) benzyl(oxy or thio), di(C$_1$–C$_3$ alkyl, C$_3$–C$_6$ cycloalkyl, or C$_4$–C$_8$ cycloalkylalkyl)amino, (mono-C$_1$–C$_3$ alkyl, C$_1$–C$_3$ alkoxy or halo)(phenyl, phenoxy, phenylthio, phenylsulfonyl or phenoxysulfonyl), C$_2$–C$_6$ alkanoylamino, benzoylamino, diphenylmethylamino (C$_1$–C$_3$ alkyl), aminocarbonyl, C$_1$–C$_3$ alkylaminocarbonyl, di(C$_1$–C$_3$ alkyl)aminocarbonyl, halo-C$_1$–C$_6$ alkanoyl, aminosulfonyl, C$_1$–C$_3$ alkylaminosulfonyl, di(C$_1$–C$_3$ alkyl)aminosulfonyl, phenyl(oxy or thio)(C$_1$–C$_3$ alkyl), (halo, C$_1$–C$_3$ alkyl or C$_1$–C$_3$ alkoxy)phenyl(oxy or thio)(C$_1$–C$_3$ alkyl), benzoyl, or (amino, C$_1$–C$_3$ alkylamino or di(C$_1$–C$_3$ alkyl)amino)(C$_1$–C$_3$ alkyl); which comprises oxidizing an arylmethylsulfide compound of the formula VIII

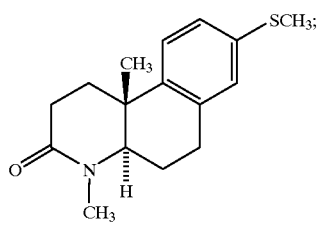
VIII to a sulfoxide compound of the formula IX

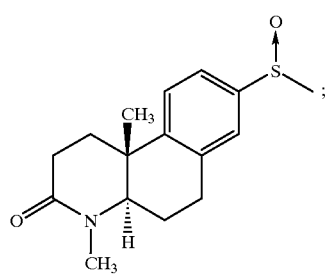
IX reacting the sulfoxide compound of the formula IX with an acylating agent to afford a Pummerer rearrangement product;

reacting the Pummerer rearrangement product with an electrophile selected from the group consisting of A-R$^1$ wherein A is a leaving group, in the presence of a phase transfer catalyst, a hydride reducing reagent and a base, to prepare a compound of the formula I.

12. The process of claim 11, wherein the acylating agent is trifluoroacetic anhydride and the Pummerer rearrangement product is a trifluoroacetyloxymethylene sulfide compound of the formula X

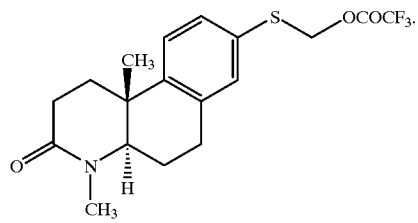
X

13. A process for preparing (+)-(4aR)-(10bR)-4-methyl-8-(4-ethyl-2-benzothiazolylthio)-10b-methyl-1,2,3,4,4a,5,6,10b-octahydrobenzo[f]quinolin-3-one, which comprises: reacting a trifluoroacetyloxymethylene sulfide compound of the formula X

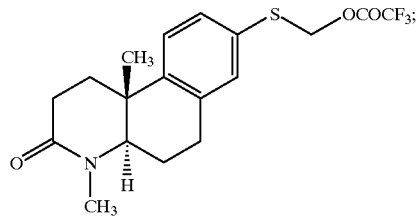
X with 2-halo-4-ethylbenzothiazole in the presence of a phase transfer catalyst, a hydride reducing reagent and a base.

14. The process of claim 11 or 12, wherein monoperoxyphthalic acid or 3-chloroperoxybenzoic acid is the oxidizing agent, 2-halo-4-ethyl-benzothiazole is the electrophile, potassium carbonate is the base, sodium borohydride is the reducing reagent and the compound prepared is (+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

15. A process for preparing a compound of the formula VIII

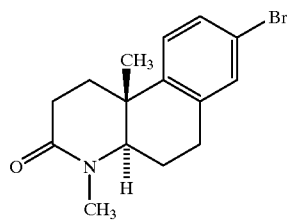
VIII which comprises reacting a compound of the formula XII

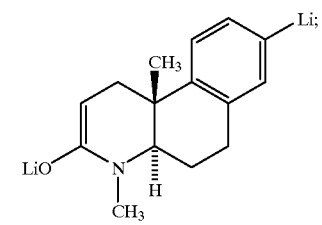
XII with a reaction mixture comprising a base and an ether solvent to afford an amide-enolate solution; reacting the amide-enolate solution with an alkyllithium compound to afford a dianion compound of the formula

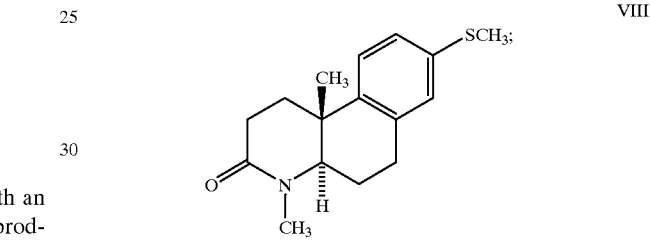

reacting the dianion compound with dimethyldisulfide to afford an arylmethylsulfide compound of the formula VIII.

16. The process of claim 15, wherein the base is lithium diisopropylamide.

17. The process of claim 15, wherein the base is lithium hexamethyldisilazide.

18. The process of either claim 16 or claim 17, further comprising adding a lithium salt and methyl lithium.

19. The process of any one of claims 15, 16, 17 or 18, further comprising converting the compound of formula VIII to a compound of the formula I

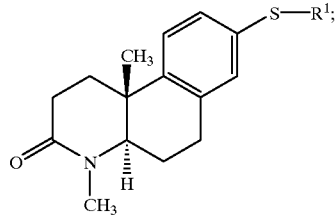

wherein $R^1$ represents:

2-nitrophenyl, 4-nitrophenyl, 2-cyanophenyl, 4-cyanophenyl, 2-nitronaphthyl, 4-nitronaphthyl, 2-cyanonaphthyl, 4-cyanonaphthyl, 2-quinolinyl, 4-quinolinyl, 7-quinolinyl, 1-isoquinolinyl, 3-isoquinolinyl, 8-isoquinolinyl, 2-quinoxalinyl, 2-benzothiazolyl, 3-1H-indazolyl, 2-benzoxazolyl, 3-1,2-benzisothiazolyl, 2-pyridinyl, 4-pyridinyl, 2-pyrazinyl, 2-naphtho[2,3-d]thiazolyl, 2-naphtho[1,2-d]thiazolyl, 9-anthryl, 2-thiazolyl, 2-benzimidazolyl, 1-benz[g]isoquinolinyl, 8-benz[g]isoquinolinyl, 5-1H-tetrazolyl, 2-quinazolinyl, 2-thiazolo[4,5-b]pyridinyl, 4-10H-pyridazino[3,2-b]-2-quinazolinyl, 2-1,4-benzodioxinyl, 2-triazine, 2-benzoxazine, 4-benzoxazine, 2-purine or 8-purine;

wherein the above $R^1$ groups are unsubstituted or substituted with 1–3 groups chosen from the group consisting of trifluoromethyl, trifluoroethoxy, $C_1$–$C_4$ alkyl, trifluoromethoxy, hydroxy, $C_1$–$C_3$ alkoxy, nitro, $C_1$–$C_3$ alkylthio, $C_1$–$C_6$ alkanoyl, phenyl, oxo, phenoxy, phenylthio, $C_1$–$C_3$ alkylsulfinyl, $C_1$–$C_3$ alkylsulfonyl, cyano, amino, $C_1$–$C_3$ alkylamino, diphenylmethylamino, triphenylmethylamino, benzyloxy, benzylthio, (mono-halo, nitro or $CF_3$) benzyl(oxy or thio), di($C_1$–$C_3$ alkyl, $C_3$–$C_6$ cycloalkyl, or $C_4$–$C_8$ cycloalkylalkyl)amino, (mono-$C_1$–$C_3$ alkyl, $C_1$–$C_3$ alkoxy or halo)(phenyl, phenoxy, phenylthio, phenylsulfonyl or phenoxysulfonyl), $C_2$–$C_6$ alkanoylamino, benzoylamino, diphenylmethylamino ($C_1$–$C_3$ alkyl), aminocarbonyl, $C_1$–$C_3$ alkylaminocarbonyl, di($C_1$–$C_3$ alkyl)aminocarbonyl, halo-$C_1$–$C_6$ alkanoyl, aminosulfonyl, $C_1$–$C_3$ alkylaminosulfonyl, di($C_1$–$C_3$ alkyl)aminosulfonyl, phenyl(oxy or thio)($C_1$–$C_3$ alkyl), (halo, $C_1$–$C_3$ alkyl or $C_1$–$C_3$ alkoxy)phenyl(oxy or thio)($C_1$–$C_3$ alkyl), benzoyl, or (amino, $C_1$–$C_3$ alkylamino or di($C_1$–$C_3$ alkyl)amino)($C_1$–$C_3$ alkyl).

20. The process of any one of claims 15, 16, 17 or 18, further comprising oxidizing the compound of the formula VIII

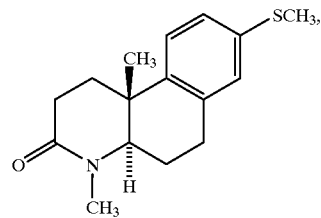

to a sulfoxide compound of the formula IX

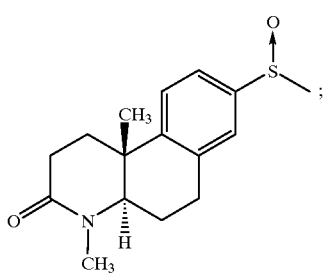

reacting the sulfoxide compound of formula IX with an acylating agent to afford a Pummerer rearrangement product; reacting the Pummerer rearrangement product with an electrophile selected from the group consisting of A-$R^1$ wherein A is a leaving group and $R^1$ represents:

2-nitrophenyl, 4-nitrophenyl, 2-cyanophenyl, 4-cyanophenyl, 2-nitronaphthyl, 4-nitronaphthyl, 2-cyanonaphthyl, 4-cyanonaphthyl, 2-quinolinyl, 4-quinolinyl, 7-quinolinyl, 1-isoquinolinyl, 3-isoquinolinyl, 8-isoquinolinyl, 2-quinoxalinyl, 2-benzothiazolyl, 3-1H-indazolyl, 2-benzoxazolyl, 3-1,2-benzisothiazolyl, 2-pyridinyl, 4-pyridinyl, 2-pyrazinyl, 2-naphtho[2,3-d]thiazolyl, 2-naphtho[1,2-d]thiazolyl, 9-anthryl, 2-thiazolyl, 2-benzimidazolyl, 1-benz[g]isoquinolinyl, 8-benz[g]isoquinolinyl, 5-1H-tetrazolyl, 2-quinazolinyl, 2-thiazolo[4,5-b]pyridinyl, 4-10H-pyridazino[3,2-b]-2-quinazolinyl, 2-1,4-benzodioxinyl, 2-triazine, 2-benzoxazine, 4-benzoxazine, 2-purine or 8-purine;

wherein the above $R^1$ groups are unsubstituted or substituted with 1–3 groups chosen from the group consisting of trifluoromethyl, trifluoroethoxy, $C_1$–$C_4$ alkyl, trifluoromethoxy, hydroxy, $C_1$–$C_3$ alkoxy, nitro, $C_1$–$C_3$ alkylthio, $C_1$–$C_6$ alkanoyl, phenyl, oxo, phenoxy, phenylthio, $C_1$–$C_3$ alkylsulfinyl, $C_1$–$C_3$ alkylsulfonyl, cyano, amino, $C_1$–$C_3$ alkylamino, diphenylmethylamino, triphenylmethylamino, benzyloxy, benzylthio, (mono-halo, nitro or $CF_3$) benzyl(oxy or thio), di($C_1$–$C_3$ alkyl, $C_3$–$C_6$ cycloalkyl, or $C_4$–$C_8$ cycloalkylalkyl)amino, (mono-$C_1$–$C_3$ alkyl, $C_1$–$C_3$ alkoxy or halo)(phenyl, phenoxy, phenylthio, phenylsulfonyl or phenoxysulfonyl), $C_2$–$C_6$ alkanoylamino, benzoylamino, diphenylmethylamino ($C_1$–$C_3$ alkyl), aminocarbonyl, $C_1$–$C_3$ alkylaminocarbonyl, di($C_1$–$C_3$ alkyl)aminocarbonyl, halo-$C_1$–$C_6$ alkanoyl, aminosulfonyl, $C_1$–$C_3$ alkylaminosulfonyl, di($C_1$–$C_3$ alkyl)aminosulfonyl, phenyl(oxy or thio)($C_1$–$C_3$ alkyl), (halo, $C_1$–$C_3$ alkyl or $C_1$–$C_3$ alkoxy)phenyl(oxy or thio)($C_1$–$C_3$ alkyl), benzoyl, or (amino, $C_1$–$C_3$ alkylamino or di($C_1$–$C_3$ alkyl)amino)($C_1$–$C_3$ alkyl);

in the presence of a phase transfer catalyst, a hydride reducing reagent and a base to prepare a compound of formula I

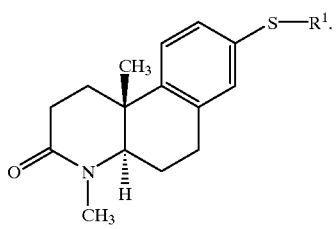

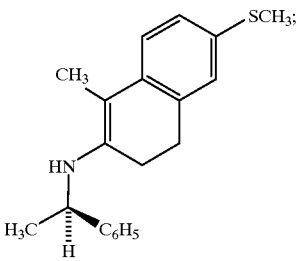

21. A process for preparing (+)-(4aR)-(10bR)-4-methyl-8-(4-ethyl-2-benzothiazolylthio)-10b-methyl-1,2,3,4,4a,5,6,10b-octahydrobenzo[f]quinolin-3-one, which comprises: reacting a compound of the formula II

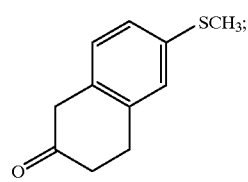

with (R)-(+)-phenethylamine to afford a compound of the formula III

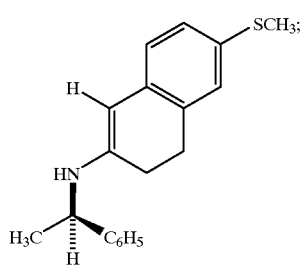

reacting the compound of formula III with a strong lithium base to afford a lithioenamine compound of the formula IV

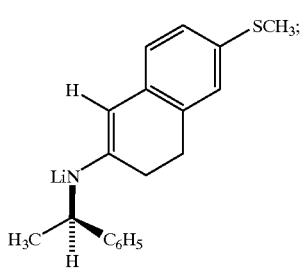

methylating the resulting lithioenamine of the formula IV to a compound of the formula V reacting the compound of formula V with an acyl halide or an anhydride of acrylic acid to prepare a compound of the formula VI

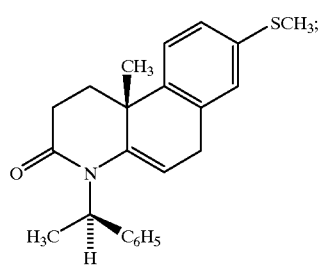

quenching the reaction with base, and combining the residue comprising the compound of formula VI with an appropriate silane and trifluoroacetic acid in the absence of a solvent to prepare a compound of the formula VII

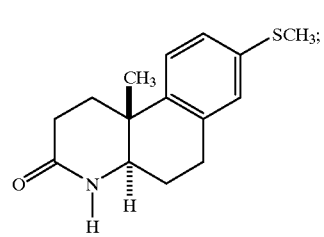

reacting the compound of formula VII with a methyl halide in a reaction mixture comprising an organic solvent and a strong base to afford an arylmethylsulfide compound of the formula VIII

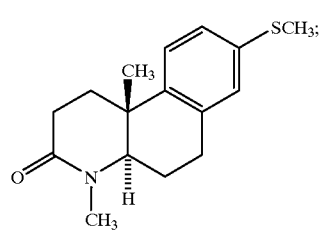

oxidizing the compound of formula VIII to a sulfoxide compound of the formula IX

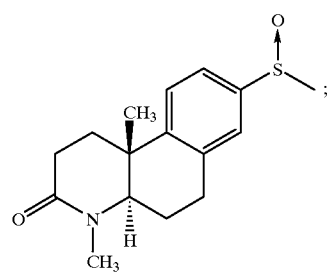

IX reacting the sulfoxide compound of the formula IX with trifluoroacetic anhydride to afford a trifluoroacetyloxymethylene sulfide compound of the formula X

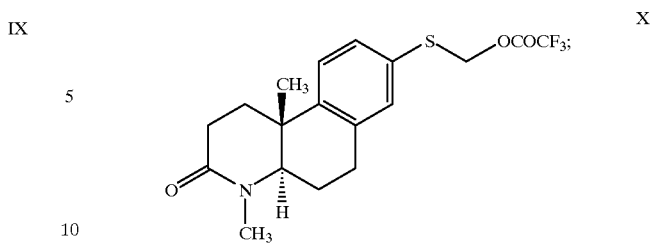

X reacting the trifluoroacetyloxymethylene sulfide compound with 2-halo-4-ethylbenzothiazole in the presence of a phase transfer catalyst, sodium borohydride and a base to prepare (+)-(4aR)-(10bR)-4-methyl-8-(4-ethyl-2-benzothiazolylthio)-10b-methyl-1,2,3,4,4a,5,6,10b-octahydrobenzo[f]quinolin-3-one.

* * * * *

UNITED STATES PATENT AND TRADEMARK OFFICE
CERTIFICATE OF CORRECTION

PATENT NO. : 6,111,110
DATED : August 29, 2000
INVENTOR(S) : John Brennan, et al.

It is certified that error appears in the above-identified patent and that said Letters Patent is hereby corrected as shown below:

In Column 31, line 4, please delete "minocarbonyl," and insert therefore --aminocarbonyl,--.

In Column 33, line 61, please delete di($C_{h1}$-$C_3$ alkyl)aminocarbonyl," and insert therefore --di($C_1$-$C_3$ alkyl)aminocarbonyl,--.

Signed and Sealed this

First Day of May, 2001

Attest:

NICHOLAS P. GODICI

*Attesting Officer*   *Acting Director of the United States Patent and Trademark Office*